US011793397B2

(12) United States Patent
Banerjee et al.

(10) Patent No.: US 11,793,397 B2
(45) Date of Patent: Oct. 24, 2023

(54) ENCAPSULATED OPTO-ELECTRONIC SYSTEM FOR CO-DIRECTIONAL IMAGING IN MULTIPLE FIELDS OF VIEW

(71) Applicant: OMNISCIENT IMAGING INC., Tucson, AZ (US)

(72) Inventors: Bhaskar Banerjee, Tucson, AZ (US);
Brian Scaramella, Tucson, AZ (US);
Richard Pfisterer, Tucson, AZ (US);
Scott Ellis, Tucson, AZ (US); Andrew Sapozink, Tucson, AZ (US);
Chih-Chiang Chang, Tucson, AZ (US)

(73) Assignee: OMNISCIENT IMAGING, INC., Tucson, AZ (US)

( * ) Notice: Subject to any disclaimer, the term of this patent is extended or adjusted under 35 U.S.C. 154(b) by 320 days.

(21) Appl. No.: 17/191,318

(22) Filed: Mar. 3, 2021

(65) Prior Publication Data

US 2021/0275004 A1  Sep. 9, 2021

Related U.S. Application Data

(63) Continuation-in-part of application No. 17/087,934, filed on Nov. 3, 2020, now Pat. No. 11,506,874.

(60) Provisional application No. 62/987,083, filed on Mar. 9, 2020.

(51) Int. Cl.
*A61B 1/04* (2006.01)
*A61B 1/00* (2006.01)

(52) U.S. Cl.
CPC .......... *A61B 1/041* (2013.01); *A61B 1/00009* (2013.01)

(58) Field of Classification Search
CPC ............................. A61B 1/041; A61B 1/00009
USPC .......................................................... 600/109
See application file for complete search history.

(56) References Cited

U.S. PATENT DOCUMENTS

| 7,801,584 | B2 | 9/2010 | Iddan | |
|---|---|---|---|---|
| 2010/0225759 | A1* | 9/2010 | Mathieu | A61B 3/1225 348/143 |
| 2013/0094095 | A1* | 4/2013 | Minefuji | G02B 13/16 359/680 |
| 2016/0088204 | A1* | 3/2016 | Liang | A61B 1/00096 348/68 |

(Continued)

*Primary Examiner* — Matthew David Kim
(74) *Attorney, Agent, or Firm* — Quarles & Brady LLP; Yakov S. Sidorin

(57) ABSTRACT

A tethered opto-electronic imaging system encapsulated in an optically-transmissible housing capsule/shell and configured to image object space in multiple fields-of-view (FOVs) to form a visually-perceivable representation of the object space in which sub-images representing different FOVs remain co-directional regardless of mutual repositioning of the object and the imaging system. The capsule/shell of the system is a functionally-required portion of the train of optical components that aggregately define and form a lens of the optical imaging system. The tether is devoid of any functional optical channel or element. When different FOVs are supported by the same optical detector, co-directionality of formed sub-images images is achieved due via judicious spatial re-distribution of irradiance of an acquired sub-image to form a transformed sub-image while maintaining aspect ratios of dimensions of corresponding pixels of the acquired and transformed sub-images. Methodology of transformation of images utilizing radial redistribution of image irradiance.

20 Claims, 16 Drawing Sheets

(56) References Cited

U.S. PATENT DOCUMENTS

| | | | | |
|---|---|---|---|---|
| 2016/0091797 | A1* | 3/2016 | Ryzhikov | G02B 13/143 |
| | | | | 356/237.2 |
| 2016/0282591 | A1* | 9/2016 | Mizusawa | G02B 13/18 |
| 2016/0338575 | A1* | 11/2016 | Honda | A61B 1/0014 |
| 2016/0345808 | A1* | 12/2016 | Inomata | A61B 1/05 |
| 2017/0199371 | A1* | 7/2017 | Williamson | H04N 13/204 |
| 2018/0252900 | A1* | 9/2018 | Cheng | G02B 9/10 |
| 2018/0310802 | A1* | 11/2018 | Gilreath | A61B 1/015 |
| 2020/0169725 | A1* | 5/2020 | Hua | G02B 27/0101 |

* cited by examiner

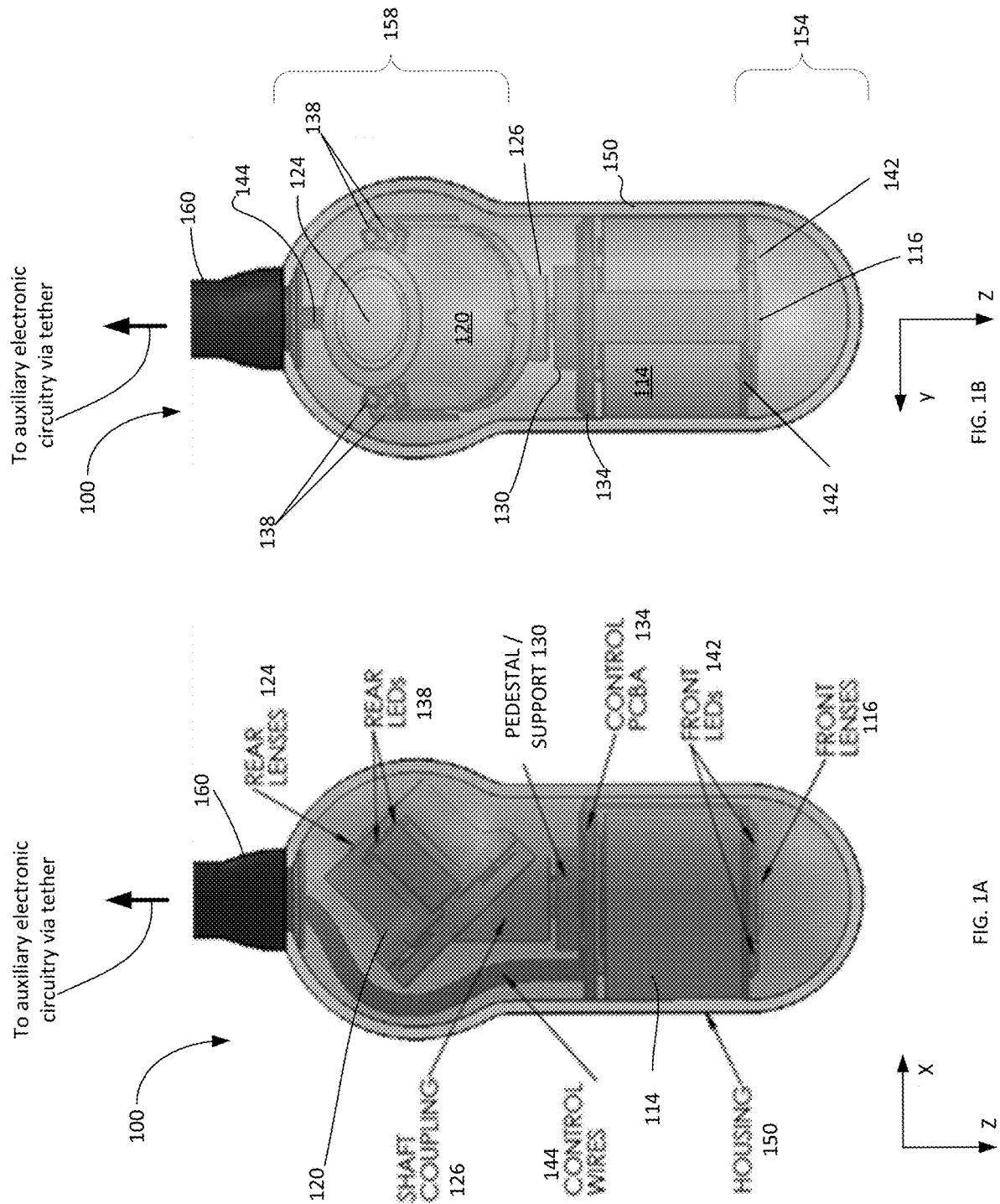

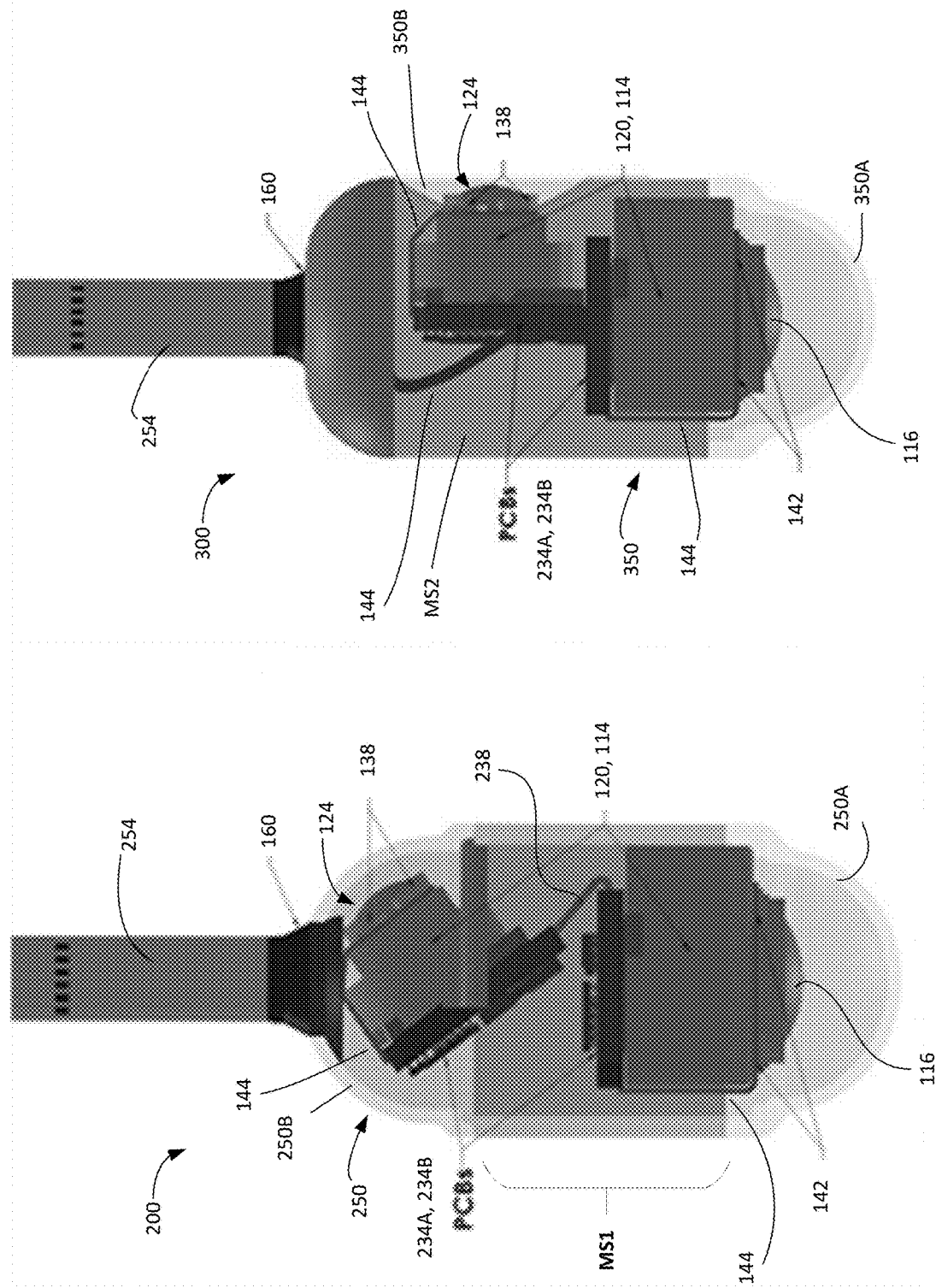

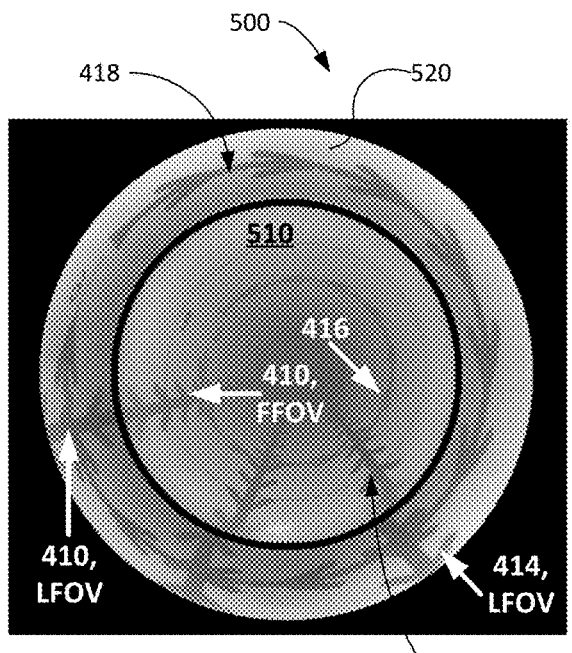
FIG. 5A
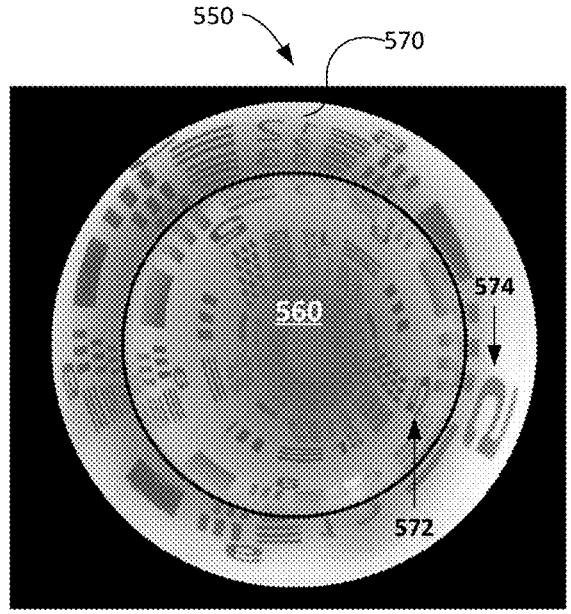
FIG. 5B
FIG. 5C
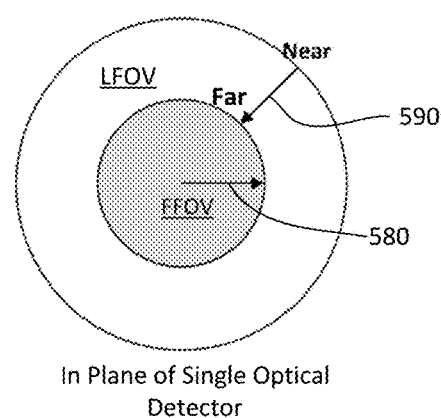
In Plane of Single Optical Detector

ENCAPSULATED OPTO-ELECTRONIC SYSTEM FOR CO-DIRECTIONAL IMAGING IN MULTIPLE FIELDS OF VIEW

CROSS-REFERENCE TO RELATED APPLICATIONS

This patent application claims priority from and benefit of the U.S. Provisional Patent Application No. 62/987,083 filed on Mar. 9, 2020. This patent application is a continuation-in-part of the U.S. patent application Ser. No. 17/087,934 filed on Nov. 3, 2020, which in turn also claims priority from the U.S. Provisional Patent Application No. 62/987,083 filed on Mar. 9, 2020. The disclosure of each of the above-identified provisional application is incorporated herein by reference.

TECHNICAL FIELD

This invention generally relates to optical imaging systems and methodologies directed to formation of optical images different portions of which may—if desired—are formed to be co-oriented and co-directional regardless of mutual repositioning of an optical imaging system and the object space. In particular, this invention is aimed at methods and apparatus configured to view a biological body cavity or organ or an inanimate space by use of a tethered imaging capsule judiciously structured to provide views of the surrounding space in two directions inside an organ in a body, container, cavity or space. Imaging feedback and control of the direction of view via the cable enables targets or areas to be imaged repeatedly and from different angles.

RELATED ART

Imaging devices for viewing identified targets inside the human body have substantially evolved from the initial systems structured a la a simple telescope. The same holds true with respect to systems configured for the inspection of pipes and other practically-important cavities (such as aircraft turbines, complex machineries and tight spaces in buildings or bridges, for example). Whereas the ability to view forward (the forward-viewing) may be preferred for navigation through the ambient surroundings, when the surroundings include tubular structures the regions of interest and related important information are more often than not located sideways or even in a backward direction(s). The ability to procure lateral (or oblique or rear) views of the object space provides the advantage of allowing structures such as the inner walls of pipes or intestines (or areas behind objects or folds in the intestinal tract, to name just a few) to be viewed substantially simultaneously (or, alternatively, on at a time) with one another and repetitively without having to change a position and/or orientation of the viewing system. Indeed, repositioning the optical system and turning backwards (as compared with the original orientation) can be difficult or even impractical to do in enclosed spaces with limited room for movement. Additionally, such required "repositioning and reorientation" understandably lengthens the time required for inspection of the target object space.

Many practical applications of imaging probes require repetitive imaging of regions located behind various obscurations. For instance, the intestinal tract, including the colon (while it can be accessed through a small opening) is not straight but highly convoluted in shape, dynamically mobile—that is, changing its shape as a function of time and biological processes occurring in the body—and has about a hundred folds that restrict the ability of the user to observe what is behind such folds. Although such views can be obtained by retro-flexing the tip of a forward-viewing scope, for example, the require operation often not physically implementable and does not provide a complete view behind the folds.

Most if not all of the imaging probes of related art (for viewing, for example, the upper gastro-intestinal tract, the esophagus, stomach and duodenum) require an endoscope/borescope/laparoscope—that is a spatially-extended imaging probe a portion of which is a rigid or flexible sheath carrying various wires, optical channels, other hardware components in its hollow and protecting these contents from the environment. The operation of a so-conventionally-structured imaging probe inevitably requires repositioning of at least a portion of the probe inside the body, which is associated with physical rotation or deviation or bending of, for example, the distal end of the sheath from or with respect to its original position. That, in turn, leads to physical impact between the probe and the physical tissue, thereby causing trauma to the bodily cavity. The viewing and associated imaging needs to be performed under sedation, which adds to the risk of traumatizing the biological tissue, is inconvenient and expensive.

SUMMARY

Embodiments of the invention provide an optoelectronic system that includes a housing shell (with a shell axis and first and second optically-transparent portions of the housing shell; each of these portions has a corresponding non-zero optical power—the first and second optical powers, respectively—and these portions are integrally connected with one another to form a wall of the housing shell that encapsulates and fluidly seals a volume); an optical detector system contained in the volume of the shell; a first lens contained in the volume of the shell and facing the first portion of the housing shell such that a combination of the first lens and the first portion of the housing shell defines and completely describes a front optical imaging system; a second lens contained in the volume and facing the second portion of the housing shell such that a combination of the second lens and the second portion of the housing shell defines and completely describes a lateral optical imaging system. Here, the front optical imaging system has a first optical axis and a front field of view (FFOV) and is configured to form a first image at the optical detector system, while the lateral optical imaging system has a second optical axis and a lateral field of view (LFOV) and is configured to form a second image at the optical detector system. At least one implementation of the optoelectronic system is structured to satisfy at least one of the following conditions a) the optoelectronic system comprises a tether electrically connecting contents of the housing shell with a programmable processor outside of the housing shell in absence of an optical channel inside the tether, and b) the first and second lens are spatially separated by the optical detector system. (In this case, at least one of the following conditions may be satisfied: (i) the tether includes only an electrically-conducting member and insulation for said electrically-conducting member, and (ii) the optical detector system includes only one optical detector.) Alternatively or in addition, the optoelectronic system can be structured such that the first image is optically-conjugate to a portion of an object space covered by the FFOV and has a first perimeter that circumscribes an axial point of the first image, while the second image is optically-conjugate to a portion of the object space covered by the LFOV and is dimensioned as a stripe or band that has a second perimeter and that is located outside of the first perimeter. Alternatively or in addition, the optoelectronic system may be structure such that the first image has a first perimeter (that is a portion of a circumference of a circle that includes an axial point of the first image and has a first radius), while the second image is dimensioned as a stripe or band having a second perimeter that is a portion of a circumference of a circle with a second radius, and wherein the second radius is no smaller than the first radius, and the optoelectronic system additionally includes programmable electronic circuitry in electrical cooperation with the optical detector system, said programmable electronic circuitry configured to govern the operation of the optical detector system and, when the optical detector system includes only one optical detector, transform a chosen image from the first and second images to form a third image such that a remaining image from the first and second images and the third image having equal directionality. Alternatively or in addition, the optoelectronic system may be configured to form the first image that is optically-conjugate to a portion of an object space covered by the FFOV (the first image having a first perimeter that is a portion of a circumference of a circle that includes an axial point of the first image and has a first radius), and the second image that is optically-conjugate to a portion of the object space covered by the LFOV (the second image being dimensioned, when the optoelectronic system is rotated in operation thereof about the shell axis, as an annulus having a second perimeter that is a portion of a circumference of a circle with a second radius, the second radius being no smaller than the first radius), while a first directionality of the first image and a second directionality of the second image are equal to one another. (Notably, in the latter case the optoelectronic system may be additionally structured to generate a visually-perceivable representation of an object space covered by the FFOV and the LFOV, where the visually-perceivable representation includes the first and second images that are radially separated by a gap, and no point in said gap optically corresponds to any of a first portion of the object space covered by the FFOV and any a second portion of the object space covered by the LFOV.)

In substantially any implementation, the first lens may include a first sequence of two meniscus lens elements, an optical doublet, and a first positive lens element separating the first sequence from the optical doublet, while the second lens includes a second sequence of a meniscus lens element and a second positive lens element. (Alternatively or in addition, two optical surfaces of the second lens may be dimensioned as aspherical surfaces, and/or an optical lens element having a first of these two optical surfaces and an optical lens element having a second of these two optical surfaces may be positioned to be separated by a positive lens element. A stop aperture of the first lens may be judiciously located between these two optical surfaces. In a related implementation, none of the lens elements from the first lens may be structured to include an aspherical surface, while a stop aperture of the first lens is located between the first sequence of the two meniscus lens elements and the optical doublet.)

In substantially any implementation, the front optical imaging system may include a sequence of three meniscus lens elements, while the lateral optical imaging system may include a sequence of two meniscus lens elements and/or none of the optical surfaces of the front optical imaging system is structured to include an aspherical optical surface. Alternatively or in addition, the optical detector system may be structured to include spatially distinct first and second optical detectors (here, the front optical imaging system is configured to form the first image at the first optical detector and the lateral optical imaging system is configured to form the second image at the second optical detector) and/or both the first and second optical detectors are positioned between the first lens and the second lens.

Embodiments of the invention also provide a method for forming an image of an object space with the use of an optoelectronic system. The method includes acquiring, with an optical detector system located inside a housing shell of the optoelectronic system that has a shell axis, a first light through a first portion of the housing shell that has a first non-zero optical power and through a first lens. (Here, a first combination of the first portion of the housing shell and the first lens defines a front optical imaging system of the optoelectronic system having a FFOV). The method also includes receiving, at the optical detector system, a second light through a second portion of the housing shell that has a second non-zero optical power and through a second lens. (Here, a second combination of the second portion of the housing shell and the second lens defines a lateral optical imaging system of the optoelectronic system having a LFOV). In implementing such method, the first and second portions of the housing shell are integrally connected with one another to form a wall of the housing shell that encapsulates and fluidly seals the optical detector system and the first and second lenses. The method further includes forming a first image of a first portion of the object space covered by the FFOV from a first output provided by the optical detector system (here, the first image has a first perimeter that is a portion of a circumference of a circle that includes an axial point of the first image that that has a first radius, the first image having a first directionality) and forming a second image of a second portion of the object space covered by the LFOV from a second output provided by the optical detector system (here, the second image has a second directionality that is equal to the first directionality.

In one specific implementation of the method, the step of forming the second image may include forming the second image dimensioned as a stripe or band having an inner perimeter and an outer perimeter, the inner perimeter being a portion of a circumference of a circle with a second radius (where the outer perimeter has a portion of a circumference of a second with a third radius, and the second radius is no smaller than the first radius and the third radius is larger than the second radius). In this case, the method may additionally include a step of rotating the housing shell about the shell axis by moving a tether that is connected to the housing shell and that lacks any optical member inside or outside the tether, in order to dimension the second image as an annulus having said second perimeter and circumscribing the first image.

In at least one implementation, the method may additionally include at least one of the following actions: transmitting electrical signals representing output from the optical detector system through a tether, which is connected to the housing shell and which is configured to transmit only electrical signals; forming an auxiliary image of the second portion of the object space covered by the LFOV, the auxiliary image having an auxiliary directionality that is opposite to the first directionality; transforming irradiance distribution of the auxiliary image to create said second image by radially redistributing irradiance of the auxiliary image with respect to a circumference of a circle of a chosen radius located between the inner and outer perimeters of said auxiliary image; and with the use of programmable electronic circuitry of the optoelectronic system, generating a report containing a visually-perceivable representation of at least one of the first image and the second image. (In such a case, the irradiance distribution of the auxiliary image includes a first irradiance at a first image pixel at a first location outside of the circumference and a second irradiance at a second image pixel at a second location inside the circumference; the first and second locations are radially-symmetric with respect to the circumference with the radius that is defined as a weighted combination of (i) a geometric mean of the second and third radii, and (ii) an arithmetic mean of said second and third radii. Here, the step of transforming of the irradiance distribution includes assigning a value of the first irradiance to the second image pixel while assigning a value of the second irradiance to the first image pixel.

At least one implementation of the method includes forming an auxiliary image of the second portion of the object space covered by the LFOV (the auxiliary image having an auxiliary directionality that is opposite to the first directionality); and transforming the auxiliary image to create said second image by radially redistributing irradiance of the auxiliary image with respect to a circumference of a circle of a chosen radius located inside an outer perimeter of said auxiliary image. Here, the radially redistributing includes exchanging of values of irradiances of first and second image pixels that are located symmetrically with respect to the circumference. In at least one implementation of the method, at least one of the following conditions is satisfied: a) the acquiring includes acquiring the first light at a first optical detector structured to collect light from the object space only through the first lens; and b) the receiving includes receiving the second light at a second optical detector structured to collect light from the object space only through the second lens. In such implementation, the optical detector system may be configured to include first and second optical detectors (respectively corresponding to the first and second lenses), while the first lens and the second lens may be positioned to be spatially separated from one another by at least one of the first optical detector and the second optical detector.

In substantially any implementation of the method, the process of acquiring may include transmitting the first light through a sequence of three meniscus lens elements prior to transmitting the first light through an optical doublet (here, the first lens comprises two of said three meniscus lens elements and said optical doublet) and/or the acquiring includes transmitting the first light through a stop aperture separating the optical doublet from a positive lens element. Alternatively or in addition, at least two meniscus lens elements from the sequence of three meniscus lens elements may be configured as negative meniscus lens elements.

In substantially any embodiment of the method, the process of receiving may include transmitting the second light through a sequence of two positive lens elements after transmitting the second light through a sequence of two meniscus lens elements (here, the second lens include one of the two meniscus lens elements and the sequence of two positive lens elements). Alternatively or in addition, at least one meniscus lens element from the sequence of two meniscus lens elements is a negative meniscus lens element.

In substantially any embodiment of the invention, the step of receiving may include transmitting the second light through first and second aspherical optical surfaces separated from one another by one lens element, and/or transmitting the second light through an aspherical optical surface of negative meniscus lens element.

BRIEF DESCRIPTION OF THE DRAWINGS

The invention will be more fully understood by referring to the following Detailed Description of Specific Embodiments in conjunction with the not-to scale Drawings, of which:

FIGS. 1A, 1B are schematic representations of an embodiment of the invention in different views.

FIGS. 2, 3 are schematic representations of related embodiments of the invention.

FIGS. 5A, 5B are images of an object space marked with indicia of FIGS. 4A, 4B, formed with an embodiment of an imaging system when both the front and lateral optical systems are serviced by the only, single optical detector.

FIG. 5C illustrates counter-directional portions of an aggregate image representing optical information acquired both in the FFOV and the LFOV of an imaging system that includes a single, only optical detector: with advancing the conventional imaging system along the optical axis, near objects are imaged to be further outwards from the optical axis, and far objects are seen located closer to the optical axis. Central portion of the image is that acquired in the FFOV; the surrounding (shown as annular) portion—that acquired in the LFOV. Portions of the image are separated with a closed planar curve. No additional transformation of the so-acquired images is conventionally carried out.

Figure 4A:
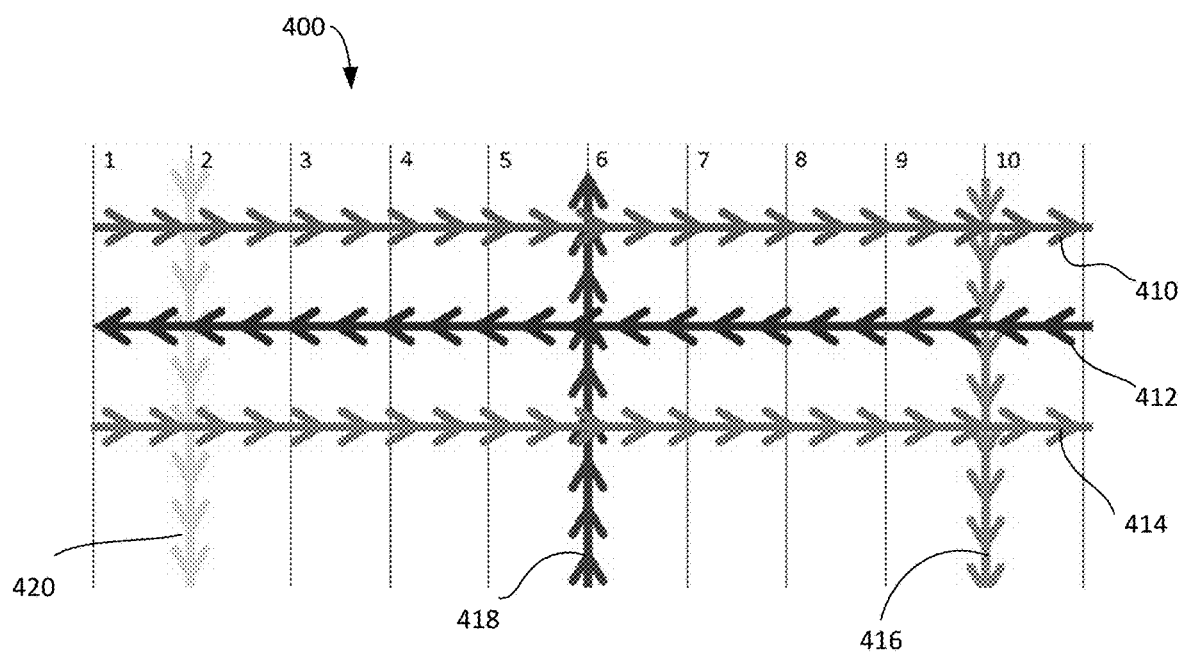
FIGS. 4A, 4B illustrate two types of indicia used for marking an object space for the purposes of optical imaging of same with various imaging systems.

Generally, the sizes and relative scales of elements in the Drawings may be set to be different from actual ones to appropriately facilitate simplicity, clarity, and understanding of the Drawings. For the same reason, not all elements present in one Drawing may be necessarily shown in another.

DETAILED DESCRIPTION

General

Embodiments discussed below—which may be interchangeably referred to as multi-view imaging devices (MVIDs)—address the remaining need for observing and/or imaging the interior portions of a body (such as esophagus, stomach, for example) in a truly nondestructive, substantially trauma-free fashion while, at the same time, delivering to a user images of the targeted object space that are truly co-directional, thereby eliminating a need for the use to analyze whether a given object feature viewed in one field of view of an MVID is, indeed, the same feature observed later in another field of view of the MVID.

The logical flow of this presentation is as follows: first, the problems solved by implementations of the idea of the invention are outlined and reference terms and conventions facilitating the understanding the scope of the invention are presented. Then, the disclosure provides details of non-limiting examples of the embodiments of the invention—both in terms of hardware and utilized methodologies of using such hardware. Finally, the disclosure offers some additional and/or alternative and/or optional considerations that may provide further insight for a person of ordinary skill in the art.

The trauma-related problem is solved by utilizing an embodiment of the present invention in which substantially all hardware components associated with and required by the operation of the embodiment are contained within a limited volume that is securely sealed from fluid or mechanically-abrasive interaction with the target tissue. This solution is achieved by configuring the imaging system of the invention inside the smooth-surfaced capsular housing unit having a tether connecting such imaging system with a point outside of the body. The capsular housing unit is dimensioned to be substantially small to be delivered to the target bodily cavity via, for example, esophagus as a result of swallowing only and not by pushing the capsulated imaging system through a bodily cavity as a result of applying a force to the tether.

In this context, it may be warranted to clearly outline the structural and/or operational difference(s) between the tethered capsule encasing the optical imaging system of the present invention and an endoscope or another imaging probe of the related art (and, similarly—between the tether itself and the sheathed or unsheathed cable of the typical imaging probe or an endoscope of the related art).

A typical endoscope is understood in the related art to be a flexible or rigid tubular—often sheathed—instrument usually containing fiber-optic element(s) through the length of the instrument (along which light is passed between distal and proximal end of the instrument) and structured to contain one or more channels or lumens throughout to enable passage of instruments (such as forceps or needles or snares) in order to visualize the interior of a hollow organ or part for diagnostic or therapeutic purposes. The light illuminating the scene to be imaged is delivered from the proximal end of the endoscope to the remote (distal) end of it via optical fibers and towards the interior of a hollow organ. A typical optical system of an endoscope is similar to that in a telescope: at the distal end, there is an objective lens optically linked to an image sensor that transmits image data via electrical wires to the proximal end of the tube and to an image processor connected to a display monito and/or. one or more of the fiber-optic element(s) or relays that carry the target-illuminating light from the proximal end of the tube to the target scene (that is, a location at the organ being imaged) at the distal end to the proximal end of the tube of the endoscope. Various related optical imaging probes are also structured in a similar fashion such as to include an optical channel or member radiationally-connecting and passing light between the proximal and distal ends of the tube/sheath of a given probe. The dimensions of the optical elements and the diameter of the tubular encasing or sheath of an imaging probe or endoscope of related art are substantially similar—on the order of several millimeters each—more often than not the optical elements of a conventional imaging probe are disposed substantially within the tubular sheath. Moreover, in all of these cases the distal end of the probe or endoscope is delivered to the target location within a bodily hollow as a result of insertion of such end into the body and pushing it by an operator to advance it into a bodily cavity or vessel as the tubular body/sheath of the conventional probe has sufficient rigidity to allow this to happen.

In stark contradistinction with related art, an embodiment of the present invention is completely devoid any optical channel between the proximal and distal ends of the embodiment, and in any case no illuminating light is passed towards the distal end from the proximal end. The capsule housing hosting and completely encasing the optical system of the invention) with a tether carrying only electrically-conducting member(s) therethrough (such as wires) simply cannot be pushed into the stomach for structural reasons—as this cable or tether lacks rigidity to push the capsule forward, into the body. Instead, the advancement of the tethered capsule towards the esophagus, for example, is dependent on participation of a conscious, cooperative patient that swallows the capsule that afterwards is advanced like a bolus of food (its movement into e.g., the stomach relies on the coordinated muscular contractions of the mouth, tongue, pharynx, and peristalsis in the esophagus, with appropriately timed relaxation of the upper and lower esophageal sphincters). A patient may take sips of water to help advance the capsule along the esophagus, to stimulate peristalsis. The tethered capsule, therefore, cannot be used in a sedated or unconscious or uncooperative patient. In contrast, advancement of an endoscope or other imaging probe of related art is not dependent on peristalsis and does not require a cooperative, conscious patient.

The natural, non-forced, and carried out without sedation propagation of the so-encapsulated imaging system through the target bodily cavity (while at least one of the available field of view of the present optical system may be reconfigured due to the natural re-orientation of the capsule and/or due to the re-orientation of the capsule via the tether) facilitates the acquisition of multiple imaging frames the compilation or separate use of which provides the user with freedom to assess the physical, structural, and/or molecular condition of the target tissue. Accordingly, embodiments of the present invention (which may also be interchangeably referred to herein as "capsules" or "tethered capsules") are structured to operate in substantial absence of (that is, while avoiding) physical disturbance and/or breach of the target biological tissue.

(A skilled artisan will readily appreciate that while wireless implementation of a "capsule" of the present invention—the ones which are not connected with any outside element or device via a tether or another mechanically-connecting member—could be used without sedation as well, the use of the wireless capsules may not be necessarily preferred as the direction, position and movement of a wireless capsule is completely (and not partially, as in the case of the tethered capsule) determined by gravity, changes in body position, muscular movements of the organ or surrounding organs or the position of the body itself. The geometric shape of each organ varies from one individual to another as well as in the same organ due to muscular contractions and movements of the body. All of these factors substantially lead to a complete loss of control what a wireless imaging capsule sees. Loss of directionality of the field-of-view, for example, can lead to lesions or pathology being missed. As an example, a wireless capsule will view the gastro-esophageal junction from the stomach only by chance, if it is randomly pointed in the necessary direction. Even so, it will only capture this view momentarily and will not be able to provide a second or repeated, confirmatory views, from a distance, or close-up.)

A skilled artisan will now appreciate that the general concept of a capsulated optical system can be also practically applied to laparoscopic or robotic handling of the optical systems, so that target areas behind the site of surgery are viewed with a rear camera inside the capsule (when multiple optically-decoupled from one another cameras are present within the same capsule) or by orienting a single, the only camera of the capsule to observe the entry of the target through a bodily wall while avoiding injury to adjacent organs or vessels.

Yet another problem persisting in related art and solved by embodiments of the invention is the inability of related art to form an optical image (of an object space) all portions of which remain co-directional upon the propagation of an imaging system of the related art down a cavity or hollow being imaged and regardless of whether these portions are the ones formed in a FFOV and/or an LFOV, and regardless of the mutual repositioning of the image-acquiring optical system and the object space. The imaging methodology of the solutions discussed in this disclosure is in stark contradistinction with the formation of an optical image achieved with the use of a conventionally-structured optical imaging system.

To this end, and for the purposes of this disclosure and recitation of claims outlining the scope of the invention—and unless expressly stated otherwise, the following terms are used:

The term "object space" is conventionally defined and understood as the space located outside of the optical imaging system in question and a portion of which—referred to as an object—is imaged through the optical imaging system onto an image surface (which may substantially coincide with a surface of an optical detector). It is the space (defined in relation to an optical system), in which the objects to be imaged by the system are located. In comparison, a space that is associated with an optical system and consists of points of which each is an image of a corresponding point in the object space—is the "image space". An object point and its image, formed with the use of the optical imaging system, are considered to be uniquely mapped to one another and, therefore, optically-conjugate to one another.

The term "optically-conjugate" and related terms are understood as being defined by the principal of optical reversibility (according to which light rays will travel along the originating path if the direction of propagation of light is reversed). Accordingly, these terms, as referring to two surfaces, are defined by two surfaces the points of which are imaged one on to another with a given optical system. If an object is moved to the point occupied by its image, then the moved object's new image will appear at the point where the object originated. The points that span optically-conjugate surfaces are referred to and defined as optically-conjugate points. A first layer or pattern is defined as being carried by (or carried on) a given surface or substrate or second layer when the first layer is directly disposed onto the given surface or substrate or second layer, or when the first layer is disposed onto an intervening third layer which, in turn, is disposed onto the given surface or substrate or second layer.

The term "image" refers to and is defined as an ordered representation of detector signals corresponding to spatial positions. For example, an image may be an array of values within an electronic memory, or, alternatively, a visual or visually-perceivable image may be formed on a display device such as a video screen or printer.

The front field of view (FFOV) of an optical system is a field of view defined by a spatially-uninterrupted solid angle such as to include the optical axis of the system and such that light incident onto the optical system from an object within this solid angle is accepted by and transmitted through the optical system to the image surface.

In comparison, the lateral field of view (LFOV) of an optical system is a field of view that is defined by a corresponding distinct solid angle that does not include the optical axis of the optical system while having light incident onto the optical system from an object within such solid angle be accepted by and transmitted through such optical system to the image surface. Notably, when a given optical system has both a FFOV and LFOV, these fields of view spatially differ from one another.

A term "positive direction of an optical axis", as used in reference to a given optical system is defined as a direction or vector representing an orientation of the optical axis from a chosen image space towards the front element of the optical system. For example, when an optical system is used in conjunction with an optical detector located behind the rear element of the optical system, the positive direction of the optical axis is the direction from the optical detector towards the front element of the optical system. (In this case, the negative direction of the optical system would be defined by a vector substantially collinear with the optical axis and pointing from the front optical element of the system towards the optical detector.)

The term "viewing angle" refers to and is defined as an absolute value (modulus) of an angle, measured with respect to and from the positive direction of the optical axis of a given optical system, at which such optical system views or observes a given object point within a FOV of the optical system.

The term "orientation" (used herein to describe an optical image formed in an image plane of the optical system in light arriving from the scene in a given FOV), refers to and is defined by one-to-one correspondence between (and corresponding mapping of) a radial position of an image point (in the optical image) with respect to the optical axis and a viewing angle characterizing an object point that is optically-conjugate with such image point.

The term "directionality" of a given optical image refers to and is defined by a direction of a change of a position of an image point, in such optical image, with respect to the optical axis as a function of a viewing angle of the corresponding object point in the object space. When such change of a position of an image point occurs in the same general direction for two images taken with the same optical imaging system, such images are considered to be co-directional.

As used in this application and unless expressly defined otherwise, the terms "lenslet" and "lens element" are defined to refer to a single, simple, structurally-indivisible and used singly optical component bound—in an axial direction—by two optical surfaces that changes the degree of convergence (or divergence, or collimation) of light passing through or traversing such component. In comparison, the terms "lens", "group of lenses", "lens system" and similar terms are defined to refer to a combination or grouping of lenslets or lens elements. Here, the optical doublet, for example, which is made up of two simple lenslets or lens elements paired together, is considered to be a lens.

Examples of Indicia for Marking Object Space to Demonstrate Operability of an Embodiment To better appreciate the problems of lack of co-orientation and/or co-directionality of images formed in different fields of view of imaging systems of related art—and, therefore, to better appreciate the solutions provided by embodiments of the invention, the reader is invited to consider a situation when a given optical imaging system is located inside a generally tubular member limiting the view of such optical imaging system. (In one practical application, this situation arises when imaging of esophagus is underway.)

As has been already alluded to above, according to the idea of the invention an embodiment of the imaging system is configured such as to have an FFOV and an LFOV and to have a first image formed in light arriving from the FFOV and a second image formed in light arriving from the LFOV be co-oriented and co-directional. As the skilled artisan will readily appreciate, the results of imaging of the judiciously-marked inside surface of the tubular member with such an optical imaging system are drastically different from the results of imaging of the same inside surface with the conventionally-configured optical system.

Figure 4B:
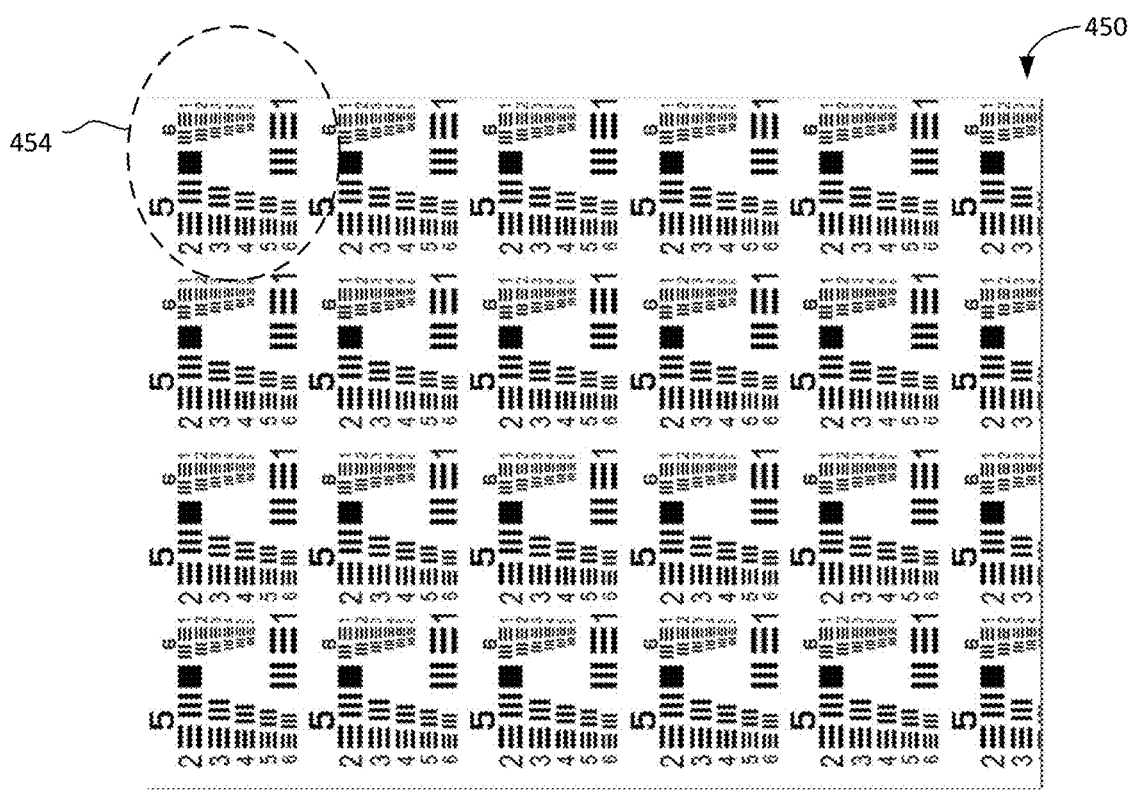

To this end, FIGS. 4A, 4B illustrate two types of indicia 400, 450, with which the inside surface of a cylindrical tube is marked in two different experiments. Each of FIG. 4A and FIG. 4B shows the markings "unwrapped" from the cylindrical inner surface of the corresponding tube onto a planar surface (by analogy with the map of the Earth presented in, for example, a Mercator Projection, with one distinct difference, however, in that the representation of the indicia 400, 450 in FIGS. 4A, 4B does not possess distortions associated with the projections typical to the projections of a sphere on a plane, as will be understood by a skilled artisan). FIG. 4A illustrates the markings 400 that contain the combination of digits 1 through 10 (oriented along the axis of the cylindrical tube and, therefore, along the positive direction of the optical axis of a given optical system inserted in such tube) and the set of arrows 410, 412, 414, 416, 418, 420, as illustrated. With respect to the inner surface of the tube, the arrows 410, 412, 414 run along the tube's axis, while the arrows 416, 418, 420 are organized in circles surrounding the tube's axis and pointing in clockwise and counterclockwise ways. FIG. 4B depicts a different type of markings 450, which represent a matrix of a indicia sub-set 454 repeated multiple times, and disposed on the inner surface of the tubular member. (The sub-set 454 in this example is but a well-known 1951 US Air Force resolution test chart, or target, and contains subsets of three lines of gradually decreasing thickness. The lines are subdivided into groups and sets. Each set consist of a subset of three vertical lines and a subset of three horizontal lines. See en.wikipedia.org/wiki/1951_USAF_resolution_test_chart for reference.) Notably, such indicia can be used with any implementation of any optical system to identify the directionality of the formed image(s).

Formation of Generally not-Co-Directional Images of the Identified Indicia.

FIGS. 5A, 5B schematically illustrate aggregate images 500, 550, formed by imaging from inside a generally tubular object space marked with, respectively, indicia 400 and 450 with the embodiment of the optical system of US 2016/0088204, for example, or by ab embodiment of the present invention in the case when the optical detector system includes only one, single optical detector to collect light from multiple fields-of-view The aggregate image 500 includes two image portions 510 (representing the imaging of the target 400 covered by the FFOV of the optical system of the related art) and 520 (representing the imaging of the target 400 covered by the LFOV of the same optical system of the related art). The arrow 416 and the digits 9, 10 are seen by the conventionally-structured optical system only in the FFOV, and therefore are imaged only into the portion 510 of the image 500. The arrow 418 and the digit 6 are viewed by the optical system of related art only in the LFOV and, therefore, are imaged only into the image portion 520. Arrows 410, 412, 414 are observed in both FFOV and LFOV and, therefore are imaged into both image portions 510 and 520 of the image 500.

It can be easily recognized that—without any judicious re-structuring of the imaging system and/or judicious transformation of the captured sub-images (image portions)—the orientation of the image portions 510, 520 are opposite to one another (as seen by the orientations of the digit 6, arrows 410, 414 in the LFOV-based image portion 520 in comparison with those in the FFOV-based image portion 510). The skilled artisan will immediately understand and appreciate that the directionalities of the image portions 510, 520 are also opposite to one another: when the optical system discussed in US 2016/0088204, for example, is moved along the optical axis inside the marked as described tubular member (the object space) in a positive direction of the optical axis, a given image point in the image portion 510 is repositioned towards the perimeter of the image field of the employed optical detector (along the arrow 580 of FIG. 5C), while another given image point in the image portion 520 is repositioned towards the center of the image field of the same optical detector (along the arrow 590 of FIG. 5C).

Similarly, the aggregate image 550 of the object space (tubular member) marked with indicia 450, formed with the conventionally-structured optical imaging system (such as the system of the US 2016/0088204, for example), includes two image portions 560 and 570. These image portions contain respective images of the object space (the inner surface of the tubular member) in the FFOV and LFOV, respectively. The different orientations of these image portions can be clearly identified by comparing spatial orientations of the elements 572, 574 of the indicia (both of which are represented by a digit 5). A person of skill will immediately recognize that—without any judicious re-structuring of the imaging system and/or judicious transformation of the captured sub-images (image portions)—the directionalities of the image portions 560, 570 are also opposite to one another. Specifically, when the conventional imaging system discussed in the US 2016/0088204 is moved along the optical axis inside the marked-as-described object space in a positive direction of the optical axis, a given image point in the image portion 560 is repositioned towards the outer perimeter of the image field of the employed optical detector (along the arrow 580 of FIG. 5C), while another given image point in the image portion 570 is repositioned towards the center of the image field of such employed optical detector (along the arrow 590 of FIG. 5C).

Implementations of an Idea of the Invention

According to the idea of the invention, an opto-electronic imaging system configured for simultaneous imaging of the object space in multiple fields of view (for example, in two fields of view including the FFOV and the LFOV) is structured to have either a single, only optical detector collecting light from the multiple fields of view or, alternatively, respectively-corresponding multiple (in this example—two) optical sensors or detectors (each forming an image of only one respectively-corresponding FOV— either the FFOV or the LFOV). The detector dedicated to imaging of the object in the FFOV is complemented with its own, respectively-corresponding optical sub-system that collects light only from the FFOV, while the detector dedicated to imaging of the object space in the LFOV is complemented with its own, respectively-corresponding optical sub-system configured to collect light only from the LFOV. According to the idea of the invention, these two optical sub-systems and the corresponding optical detectors are spatially-distinct from one another such that light acquired by the overall optical imaging system from the FFOV passes through optical elements that do not interact with light acquired by the overall system from the LFOV, and vice versa. Aggregately, the sub-systems are encapsulated in a fluidly-sealed housing at least two portions of which are dimensioned to operate as optical components that are parts of optical trains of imaging optics of the corresponding sub-systems.

Figure 14A:
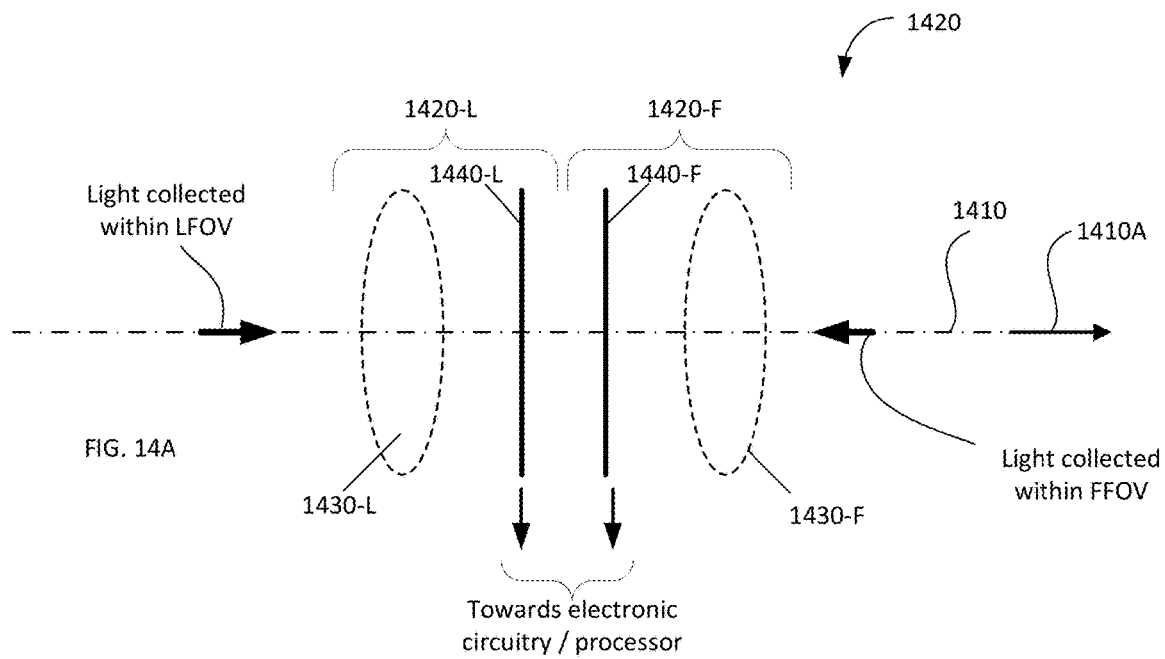
FIGS. 14A, 14B are schematic illustrations of embodiments of the invention employing a single-sensor design of the opto-electronic imaging system, and configured to spatially separate light acquisition in the FFOV from light acquisition in the LFOV.
Figure 14B:
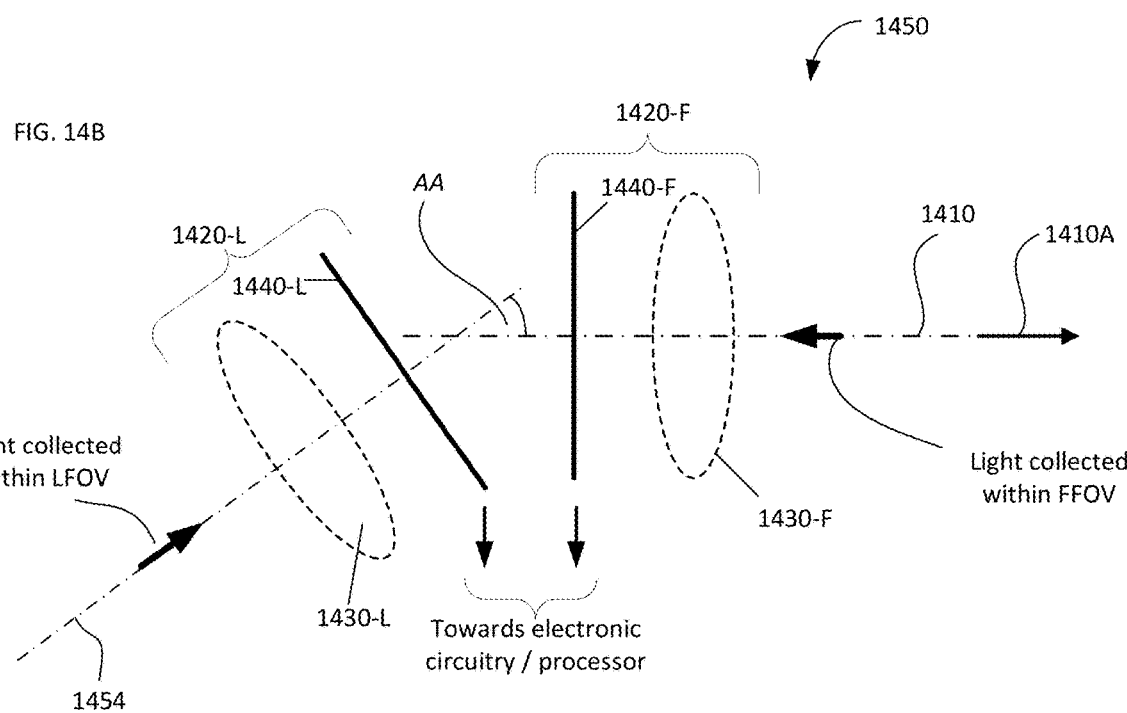

A couple of non-limiting schematic illustrations are presented in and discussed in reference to FIGS. 20A, 20B. FIG. 20A of the U.S. Provisional Patent Application No. 62/987,083, and now are shown in FIGS. 14A, 14B. FIG. 14A, for example, illustrates the embodiment 1420 with the axis 1410 (a positive direction of which is denoted with the arrow 1410A). The two sub-systems 1420-F (configured to collect light from the FFOV of the system 1420) and 1420-L (configured to acquire light from the LFOV of the system 1420) are disposed substantially co-axially, and each is formed by a corresponding lens (or lens system) and a corresponding optical detector: (1430-F, 1440-F) and (1430-L, 1440-L), respectively. Each of lenses 1430-F, 1430-L is shown schematically, in the most general form in dashed lines, and may include one or more lenslets of lens elements. FIG. 14B contemplates a related structure 1450, in which the rear portion 1420-L of the imaging system and the front portion 1420-F of the imaging system are not co-axial: the respectively-corresponding local optical axes 1454 and 1410 are inclined with respect to one another at an angle AA (which may be chosen based on other operational characteristics of the system, and can generally range from zero to a maximum value that is limited by the condition of the LFOV not overlapping with the FFOV).

A skilled artisan will readily appreciate that, generally, the sub-systems 1420-L and 1420-F may be structured to possess different optical and/or geometrical characteristics, and, depending on the goals of the particular design, provide different spatial resolution, different lateral magnification, etc. (Examples of specific implementations of the optical trains of the imaging system of the invention are discussed below.)

In s specific case when the embodiment includes only one, single optical detector to collect light form both the FFOV and the LFOV, upon the acquisition of the sub-images from the FFOV and the LFOV, the electronic circuitry of an embodiment of the invention appropriately transforms at least one of the sub-images with the use of a programmable processor (which may be configured to be a part of the overall imaging system) to generate a final set of sub-images that are co-oriented and/or co-directional, and to present and/or store the so-transformed sub-images as one aggregate image or separately, as required. (Since a skilled person will readily appreciate how an embodiment of the opto-electronic imaging system of the invention that includes only one, single optical detector differs from an embodiment in which each of the multiple optical imaging systems is supported by a dedicated, respective optical detector—the examples of FIGS. 1, 2, and 3 are addressing only the latter situation.)

FIGS. 1A and 1B are generalized schematic representations of one non-limiting specific implementation of the idea of the invention in different views.

Here, the opto-electronic system 110 of the embodiment (also referred to as a tethered capsule, although the tether itself is shown but only indicated) 100 includes a front sub-system (or camera) 114 equipped with a lens system 116 (that is configured to form an image of the scene in a front field of view (FFOV) and a rear sub-system (or camera) 120 equipped with a lens system 124 (that is configured to form an image of the scene in a lateral field of view (LFOV). The front and rear opto-electronic sub-systems are moveably connected with a shaft coupling 128 (which, in one specific case, may be judiciously structured to possess degrees of spatial repositioning and/or re-orientation sufficient to move the rear sub-system 120 along at least one of the chosen axes x,y,z of the local system of coordinates and/or radially along a radius R and/or in angular space—whether azimuthally, or altitude-wise (that is, latitude-wise), or any combination thereof with respect to the predetermined center-of-rotation COR, to provide for the instantaneous LFOV. The shaft 128 may be attached to a transitional pedestal/support element, connecting it to the electronic circuitry 134 operably cooperated with both the front and a rear sub-systems 114, 120.

In one implementation, the front sub-system 114 is configured to remain substantially stationary (with respect to the housing 150), such that the FFOV defined by the lens system 116 is axially-centered on the z-axis and/or the rear sub-system is also configured to remain substantially stationary (with respect to the housing 150), while the electronic circuitry 134 is disposed between the front and rear subsystems 114, 120 and is electrically connected to both.

Each of the rear and front sub-systems is equipped with the locally-disposed sources of light or emitters, indicated in FIGS. 1A, 1B as rear and front LEDs 138, 142. While the emitters 138, 142 are shown to be present only in a couple of pre-determined location in the proximity of the outer surfaces of the lens systems 124, 116, the skilled artisan will readily appreciate that in at least of related embodiment the series of numerous emitters can be used disposed to substantially circumscribe the periphery of the corresponding lens system 124, 116.

Electrical signals are exchanged between the circuitry 134 and the proximally-located auxiliary electronic circuitry (which may, in at least one implementation be further cooperated with a monitor or display configured to generate a visually-perceivable representation of the scene being imaged with the lens systems 116, 124) via a thin tether containing a flexible electrically-conducting member therein (a wire or flex circuit 144, for example) or wirelessly (in which case the tether is configured to provide but only a mechanical connection between the embodiment and the auxiliary point of reference—for example, the user).

The combination of the front and rear optoelectronic sub-systems 114, 120, the associated circuitry 134, and a portion of the wire 144 (when present) are encapsulated in the elongated housing (or housing shell, or capsule) 150, at least proximal (rear) and distal (front) portions 154, 158 of which are made of optically-transparent material transmitting light at the wavelength(s) of interest to imaging the target scene with the lens systems 116, 124.

The encapsulated in the housing 150 components are preferably made substantially sealed against the penetration of a fluid, in which case the appropriate collar-seal/strain-relief collar 160 may be used to accommodate the tether in case the tether is carrying any electrical member that, in operation, transmits electrical signal(s).

In at least one implementation—as shown—at least one of the rear and front portions 154, 158 of the housing 150 is judiciously dimensioned to have a non-zero curvature. In one specific case (as shown), at least one of the portions 154, 158 contains a substantially hemispherical cap, while in a related embodiment the surface(s) of at least one of the portions 154, 158 may include aspherical surfaces. In one case, the shapes of the inner and/or outer surfaces of at least one of the optically-transparent portions 154, 158 of the housing 150 are judiciously designed to configure such portion(s) as refractive optical component(s) that, together with the respectively-corresponding lens systems 116, 120 take part in forming image(s) of the target scene in LFOV and/or FFOV at the optical detectors contained at the image planes of the lens systems of the opto-electronic sub-systems or cameras 114 (forward looking camera, with FFOV), 120 (laterally looking camera, with LFOV). An optical additional mechanical harness—present when and if required for affixing the contents of the volume of the housing shell or capsule 150 inside the housing shell or capsule 150—is not shown for simplicity of illustration.

With the benefit of this description, the skilled artisan will now readily appreciate that the embodiment 100 is generally structured include a 2-sensor, 2-lens assembly tethered capsule that can be used, retrieved and used repeatedly to examine body cavities or organs such as the esophagus, stomach and intestines. The tether functions to not only transmit power and return images, it further serves to allow the capsule to be rotated along its longitudinal axis to enable the rear-camera to view a full 360 degrees along the azimuth. The outer capsule/optically transparent shell houses two sets of lens elements and two respectively-corresponding 5MP sensors for viewing forwards and obliquely backwards with fields of views of 140° (FFOV) and 100° (LFOV). The respectively-corresponding portions of the shell are dimensioned to operate as additional lens elements that not only are parts of the corresponding optical trains of FFOV- and LFOV-imaging optics (without the presence of which the corresponding FFOV-based and LFOV-based images are not generated) but that also are integrally connected to one another as portions of one single, unitary, and in specifically case structurally indivisible housing shell. Both these fields of view can be changed to as much as 180°. The tether allows the capsule to be manually rotated to get a 360-degree view of lateral or rear structures, such as the gastro-esophageal junction if the capsule is positioned in the stomach.

The embodiment 100 is structured to generally satisfy at least one of the following operational conditions:

1. The collected "instantaneous" lateral views (corresponding to optical snap-shots acquired by the rear (or laterally-looking) camera 120 at each of its spatial positions can be assembled/stitched into a continuous annular lateral view.

2. At least one of the controlling electronic circuitry 134 and/or the auxiliary electronic circuitry at the receiving end of the communications between the capsule 100 is configured to ensure that the stitched, continuous annular lateral-view and the forward-view images acquired with the cameras 114, 120 can be displayed together as a single image such that the annular lateral-view surrounds the forward view, consistent with the position and direction of the forward-view.

3. The processor operably associated with the live display of images, acquired in the front and lateral FOVs, may be appropriately programmed to position the constituent images relative to each other in an intuitive way.

4. Any of the lens systems 116, 124 may optionally be configured as a zoom lens, as is known in the art.

5. Illumination can be external (not shown) or internal from within capsule (see LEDs 138, 142, with white light, as well as monochromatic from UV to IR, or with any part of the electromagnetic spectrum.

FIGS. 2 and 3 present general schematic diagrams of related practical implementations of the tethered encapsulated imaging system configured according to the idea of the invention.

The embodiment of FIG. 2, electro-optical sub-systems 114, 120 again include forward-looking and laterally-looking (obliquely oriented or rear) cameras that contain front and rear camera lenses 116, 124, respectively. The respectively-corresponding to these cameras two optical sensors or detectors are mounted on PCBs 234A, 234B and attached to the holders of the sub-systems 114, 120 to capture the images of the targeted ambient from the FFOV and LFOV and along the optical axes of the front and rear lenses 116, 124 that are not perpendicular to one another. The front and rear sub-systems 114, 120 are cooperated with one another via a connecting member 238 which carries therethrough or thereon a portion of the connecting signal wire(s) (or, signal flex circuit) 144. Illuminating the FFOV and LFOV LEDs 142, 138 are mounted at the front of the corresponding lens holders. The capsular housing 250 has a (optionally, non-optically-transparent, opaque) generally tubularly-shaped middle section (schematically marked as MS1), and two optically-transparent dome-like sections 250A, 250B each of which possess a non-zero optical power, each of which is configured to function as part of the optical imaging system corresponding, respectively, to the sub-systems 114, 120, and each of which transmits light in an optically-imaging fashion towards the lenses 116, 124 respectively. It is understood that each of the dome-like sections 250A, 250B is structured an optical lens element in absence of pre-determined optical properties of which from the embodiment 200 the optical images that are optically-conjugate to the portions of the object space covered by the FFOV and the LFOV simply cannot be formed at corresponding optical detectors. Each of the FFOV and the LFOV of the embodiment 200 depends on the optical properties of the lens elements 250A, 250B, respectively. The portions 250A, 250B of the outer housing shell 250 are structurally connected to one another as two parts of the wall of the shell 250 to form a single, unitary shell 250. The flexible tether/cable 254 devoid of any functional optical channels is cooperated with the body 250 with the use of a strain relief element 160. In at least one implementation, the tether has distance marks on it (identifying, for example, 1 and/or 5 cm intervals) to for the user to be able to measure a distance/position of the shell 200 with respect to a reference point and/or dimensions of lesions such as incisors from the reference point during the operation of the embodiment. The outer casing 250 is sealed and fluid-proof.

A related implementation 300 is illustrated in FIG. 3, which shows that the PCBs 234A, 234B respectively corresponding to the front and rear sub-systems 114, 120 are physically attached to one another at a substantially right angle such that the optical axis of the rear lens 124 is substantially perpendicular to the optical axis of the front lens 116. The PCBs 234A, 234B are operably connected to the respectively corresponding optical sensors (not explicitly shows, as hidden in 114, 120). LEDs 142, 138 are mounted at the front of the corresponding lens holders. By analogy with the design of the embodiment of FIG. 2, the capsular body 350 has front and lateral optically-transparent and possessing non-zero optical power portions 350A, 350B through which light from the FFOV and LFOV respectively is collected by the lenses 116, 124 and which are parts of the overall optical system of the front and rear sub-systems 114, 120. It is understood that the sections 350A, 350B are structured as optical lens elements in absence of pre-determined optical properties of which from the embodiment 300 the optical images that are optically-conjugate to the portions of the object space covered by the FFOV and the LFOV simply cannot be formed. Each of the FFOV and LFOV of the embodiment 300 depends on the optical properties of the lens elements 350A, 350B. A portion of the capsular body 350 may be formatted as a central (and optionally opaque) housing section schematically marked as MS2 that, in this case, contains the optically-transparent window 350B. The window 350B covers only a limited portion of the peripheral area of the capsular body 350 and which is judiciously aligned with the LFOV of the lens 124 in a spatially-fixed fashion to be a part of the overall optical system of the sub-system 120. The portions 350A, 350B of the outer housing shell 350 are structurally connected to one another as two parts of the wall of the shell 350 to form a single, unitary shell 350. The flexible tether 254 is operably cooperated with the body 350 and its contents with the use of the strain relief 160. In at least one implementation, the tether has distance marks on it (identifying, for example, 1 and/or 5 cm intervals) to for the user to be able to measure a distance/position of the shell 200 with respect to a reference point and/or dimensions of lesions such as incisors from the reference point during the operation of the embodiment. The outer casing 350 is sealed and fluid-proof.

Example 1 of an Optical System Used with an Embodiment of the Invention

Several notes are in order concerning a particular embodiment of the utilized lens systems. Table 1.1 summarizes data representing optical train (sequence) 600 of lens elements schematically shown in FIG. 6, forming the front optical imaging system of the embodiment of the invention (for example, embodiment 100, 200, 1450), and used for imaging of the ambient space in the FFOV. The local optical axis of the lens system is denoted as 604. Table 1.2 summarizes data representing optical train (sequence) 1000 of lens elements schematically shown in FIG. 10 and forming the rear optical imaging system of the embodiment, and used for imaging of the ambient space in the LFOV. The local optical axis of the lens system is denoted as 1004.

As a skilled artisan having the benefit of this disclosure will readily understand, in the discussed example, the front optical imaging system (shown as 600 in the implementation of FIG. 6) includes the lens element 250A configured as a portion of the outer shell/capsule of the embodiment and the front lens 116 that includes 5 lens elements, to provide an aggregate 140° front field of view and imaging resolution of about 50 μm in a direction transverse to the local axis of the front lens 116. The rear optical system (shown as 1000 in the example of FIG. 10) includes the lens element 250B configured as another portion of the outer shell/capsule and the rear lens 124 (that includes 3 lens elements), to provide aggregately a 100° lateral field of view and transverse resolution of about 100 μm. Generally, the lens elements can be made of plastic polymers, such as E48R and OKP4HT, or can be made of glass. In this iteration, there is an f # of 4.5. For use in the esophagus and stomach, the optics are designed to provide optimum imaging performance over the range of distances expected in the esophagus and upper stomach from as close as 2 mm away and as much as 10 cm away from the capsule with the overall Modulation Transfer Function (MTF) defined to ensure a nearly diffraction-limited performance at a working distance of 8 mm from the capsule. The substantially hemispherical dome portions of the capsule/shell of the embodiment of the overall opto-electronic system can be diamond turned or injection molded and made from transparent plastic, such as Polymethyl methacrylate (PMMA) in one specific non-limiting example.

Non-Limiting Example of a Front Optical Imaging System.

Figure 6:
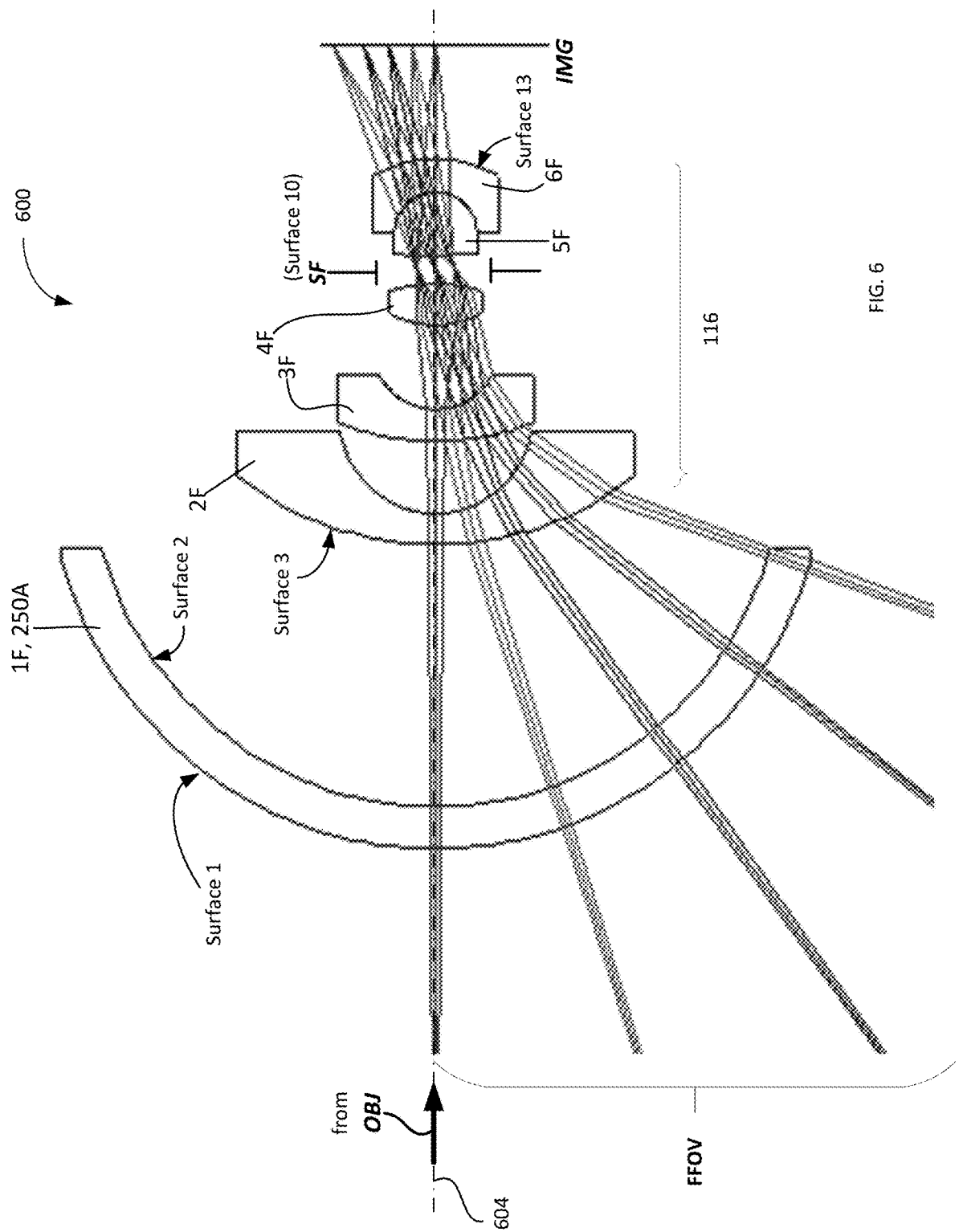
FIG. 6 provides a schematic of an optical train of a lens configured to image a portion of the object space covered by the FFOV (such as lens 116 of an embodiment of FIGS. 1, 2) of the imaging system of an embodiment of the invention.

In reference to Table 1.1 and FIG. 6, describing the embodiment 600 of the front optical imaging system (or lens system) that is characterized by an f-number of about f/4.4, the numbering of the individual optical elements and optical surfaces is specific to FIG. 6 only. Not all surfaces of all lens elements are expressly indicated. Light within the range of viewing angles of the system 600 that corresponds to the FFOV arrives along the local optical axis 604 at the front surface of the lens element 1F, 250A (specifically, at the surface 1 of the design, see Table 1.1) that is configured to transmit this light through the lens element 1F, 250A with the axial thickness of 0.5 mm, through the surface 2, and towards the lens element 2F (which is bound by the surfaces 3 and 4, respectively). Upon sequentially traversing the lens elements 3F and 4F, the light from the FFOV arrives at the surface corresponding to the aperture stop SF (which is surface 10 of the current embodiment, separated by about 0.192 mm from the lens element 4 and by about 0.155 mm from the lens element 6). Having passed through the aperture stop SF, light from the FFOV traverses the optical doublet formed by the lens elements 5F and 6F, eventually forming an image IMG of the portion of the object space covered by the FFOV on the surface of the optical detector of the sub-system 114.

In the notation used in Table 1.1, positive radius value for a given surface indicates that the center of curvature of such surface is to the right of the surface, while a negative radius value indicates that the center of curvature is to the left of the surface; dimensions are provided in millimeters; thickness is defined as an axial distance from a given surface to the next surface; and an indicated image diameter is a paraxial value and not a ray-traced value. Furthermore, with respect to decentering constants (if any), a decenter defines a new coordinate system (displaced and/or rotated) in which subsequent surfaces are defined. In such a case, surfaces following a decenter are aligned on the local mechanical axis (z-axis, for example) of the new coordinate system. The new mechanical axis remains in use for referencing purposes until expressly changed by another decenter. The order in which displacements and tilts are applied to a given surface is specified using different decenter types and these generate different new coordinate systems; those used in this disclosure are explained below. Alpha, beta, and gamma values are presented in degrees. Aspheric surfaces, if any, are labeled as A(i), and the aperture stop is denoted as S.

As shown in the specific example of FIG. 6, light arriving to the front surface (as shown—surface 3) of the front lens 116 from the FFOV through the passes through the first group of lens elements represented by a sequence of two negative meniscus lens elements 2F, 3F. Immediately prior to impinging on the image surface IMG, the same light traverses a second group of lens elements represented by the optical doublet 5F,6F, which is separated from the first group of lens elements by a positive lens element 4F. The optically-transparent portion or "dome" 250A of the housing shell is dimensioned as yet another negative meniscus 1F. Having the advantage of understanding of the practical limitations on operation of the lens 600 (among which there is an extremely short working distance), the skilled person will now readily appreciate that the use of only one meniscus lens between the "dome" 250A and the image plane is simply not sufficient to quickly enough reduce the angles of propagation of light arriving from the periphery of the desired FFOV. The use of the two meniscus lens elements 2F, 3FG, however, leads to lots of aberrations that have to be corrected by the following positive lens element 4F. The use of the optical double 5F, 6F corrects color aberrations.

Figure 7:
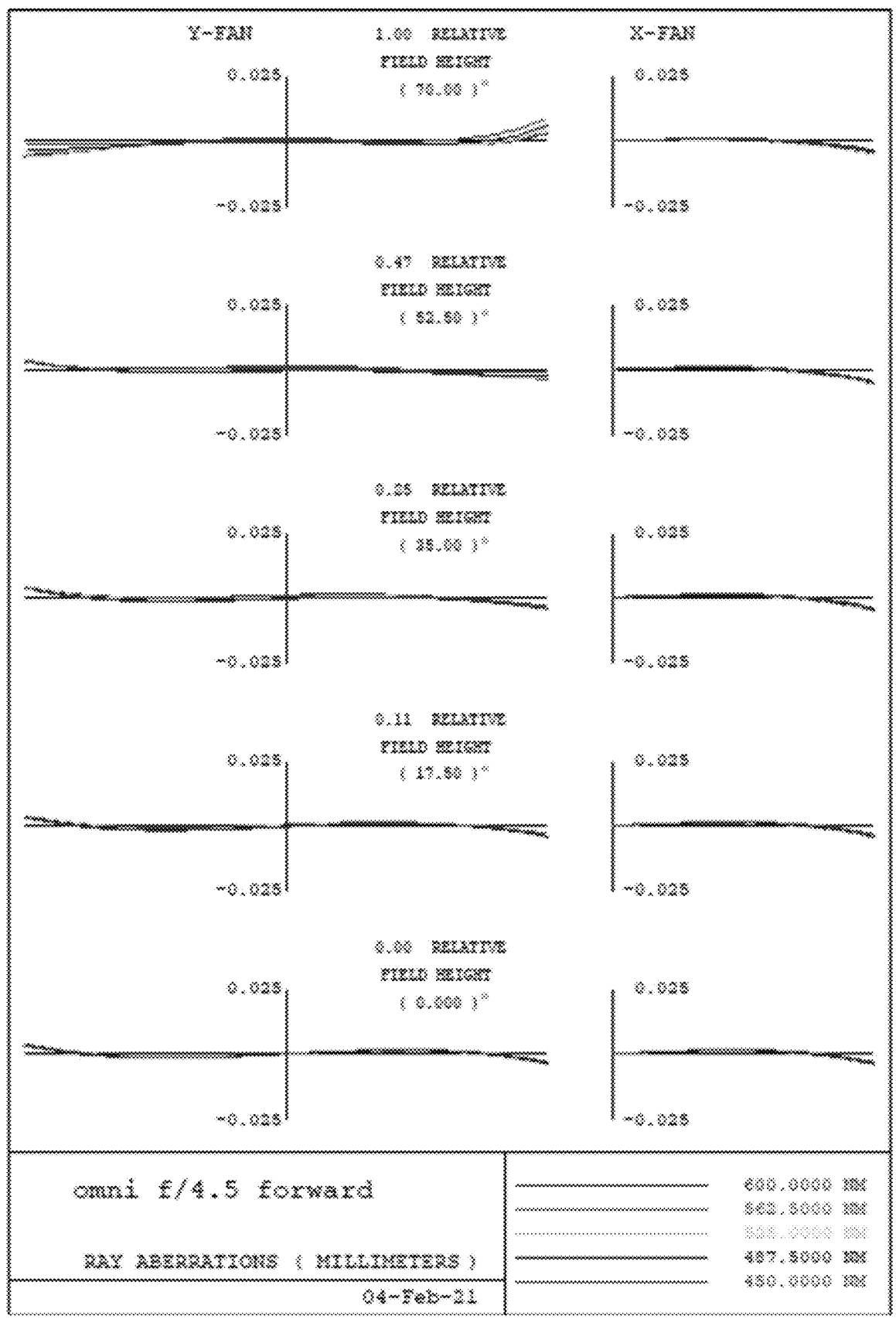
FIG. 7 provides description of transverse ray aberrations during the optical imaging in the FFOV through the lens of FIG. 6.
Figure 8A:
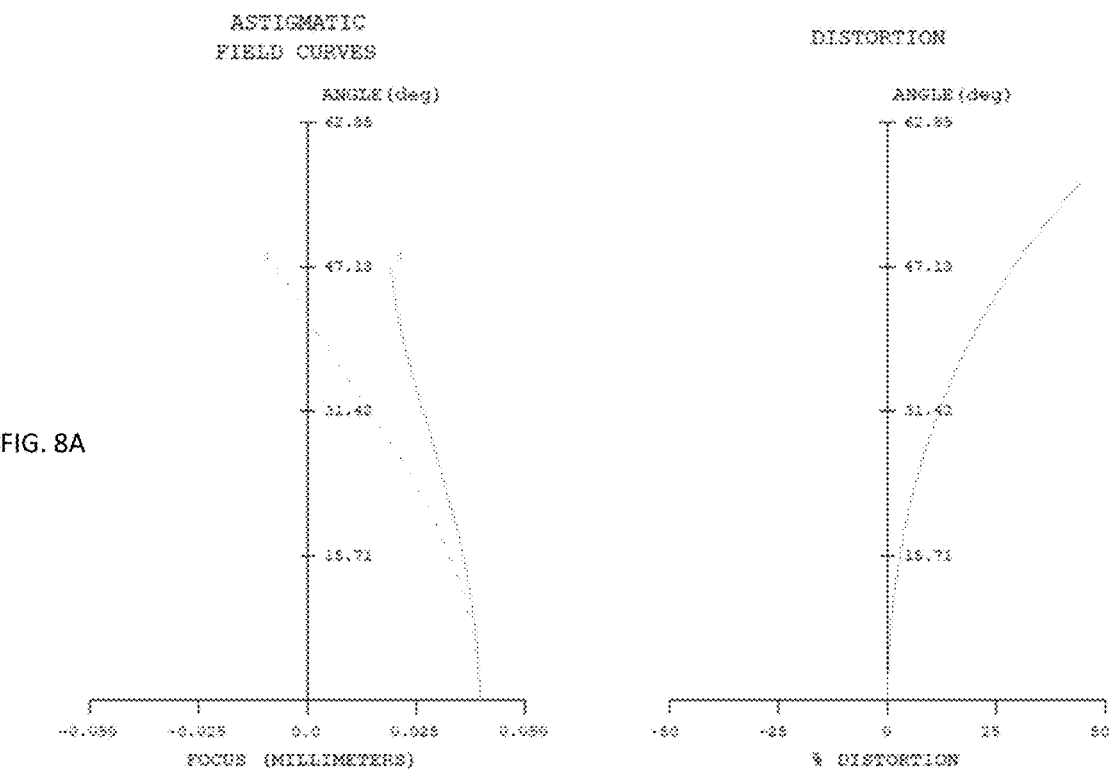
FIGS. 8A, 8B illustrate field curves, distortion characteristics, and the spot diagrams associated with the practical use of the embodiment of FIG. 6 during imaging of the object space in the FFOV only
Figure 8B:
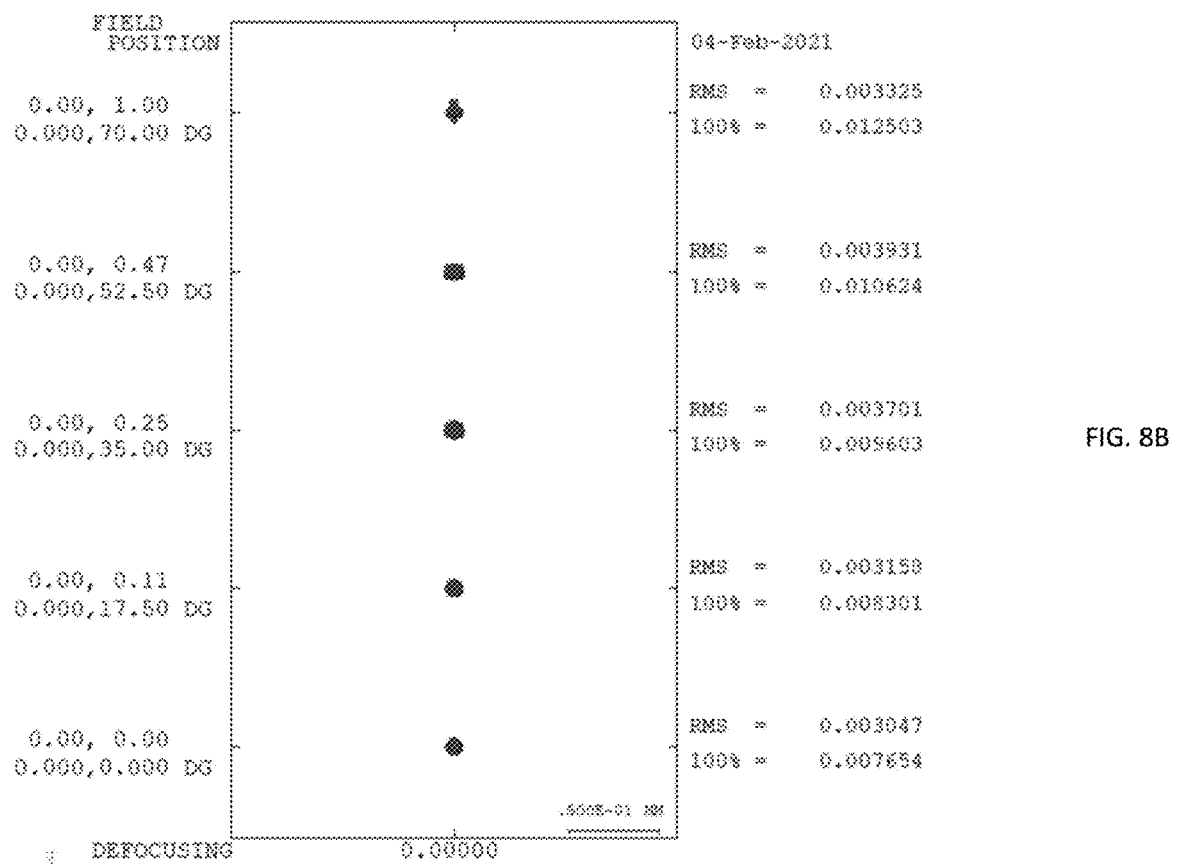

And such corrections are operationally sound. FIG. 7 illustrates transverse ray aberrations representing optical performance of the embodiment 600 during the imaging of the object space in the FFOV: these aberrations are substantially below 10 microns for any field up to 70 degrees (which represents the relative field height of unity) for light at any of wavelengths of 450 nm, 487.5 nm, 525 nm, 562.5 nm, and 600 nm, and substantially below 5 microns for any field up to at least 52 degrees (which represent the relative field height of 0.47) for light at any of the same wavelengths. FIG. 8A illustrates the corresponding field curvature and distortion characteristics as a function of field angle. The distortion figure, for example, is notably within only 5% for field angles up to about 16 degrees, and within less than 10% for field angles up to about 30 degrees. The spot diagrams, illustrated in FIG. 8B, boast the rms spot size below about 3.3 microns for imaging at the full field height (field of 70 degrees) and of about 3 microns form imaging the axial portion of the object in the FFOV.

Figure 9:
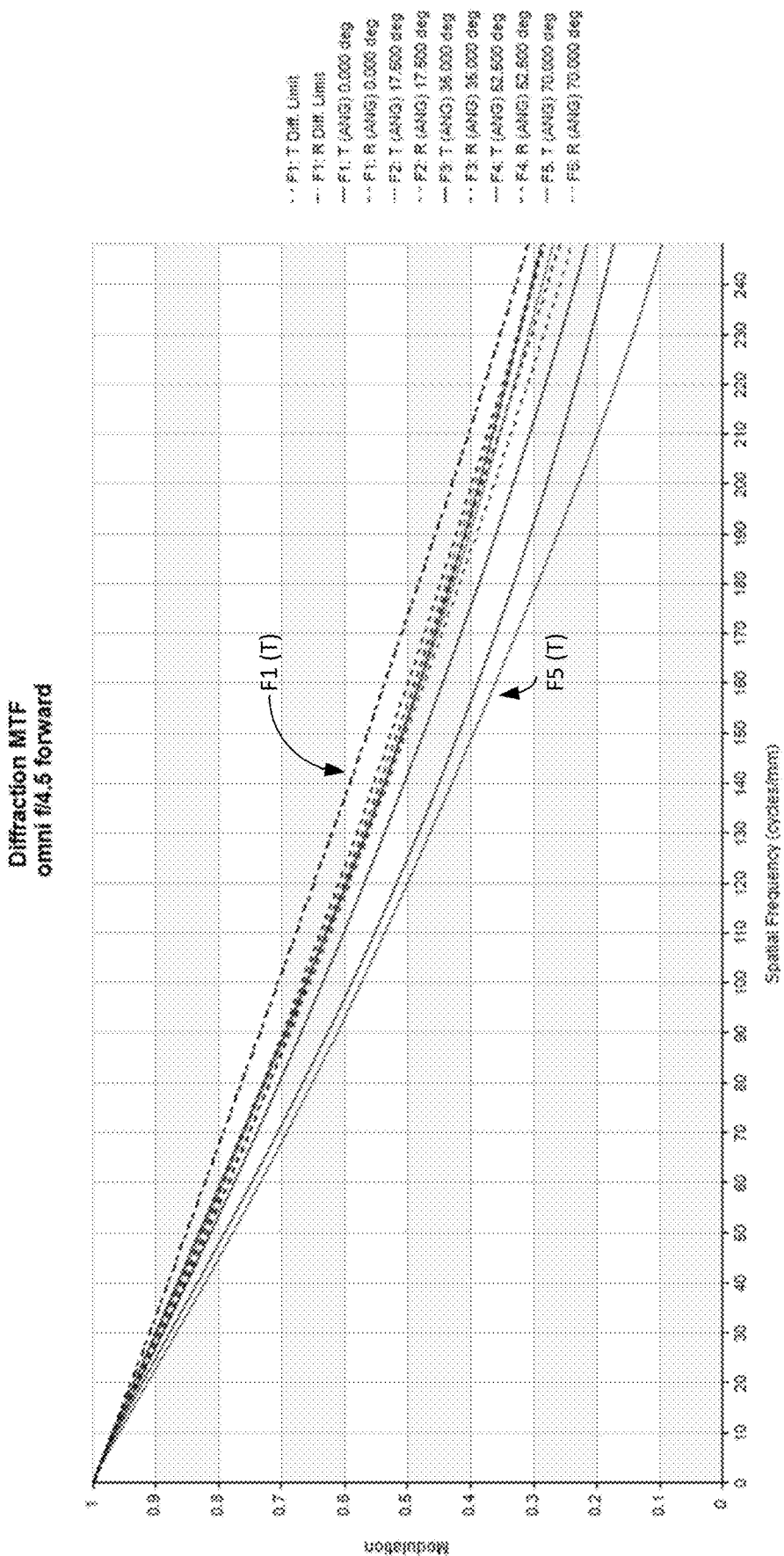
FIG. 9 presents the curves of the modulated transfer function (versus field) for the embodiment of FIG. 6 that characterizes the optical imaging in the FFOV only.

For assessing other types of aberrations, the identification of what is practically acceptable comes down to the modulated transfer function (MTF) curves. Based on the proposed design and in reference to FIG. 9 (that illustrates parameters of the MTF characterizing the operation of the embodiment 200 in the visible portion of the spectrum in the FFOV), the ideal solution is substantially close to being diffraction-limited (the top curve among the MTF curves). Notably, the performance of the design on-axis is close to the ideal solution, with some falloff at the edge of the field—and would be considered practically acceptable by a person of ordinary skill in the art in visual and/or photographic optical systems. Specifically, the cut-off frequency of operation in the visible portion of the spectrum is always way above 240 cycles/mm (both for imaging in tangential and sagittal planes) for any field up to the elative field height of unity (corresponding to 70 degrees).

TABLE 1.1.

| ELEMENT NUMBER | SURFACE DESCRIPTION RADIUS OF CURVATURE | | SEPARATION or THICKNESS | APERTURE DIAMETER | | MATERIAL |
| --- | --- | --- | --- | --- | --- | --- |
| | FRONT | BACK | | FRONT | BACK | |
| OBJ (object) | 11.6440 | | 8.0000 | | | AIR |
| 1F | 4.6300 CX | 4.1300 CC | 0.5000 | 8.9555 | 8.0053 | ACRYLIC |
| | | | 3.1440 | | | AIR |
| 2F | 3.8370 CX | 1.1539 CC | 0.3750 | 4.3400 | 2.2820 | E48R Zeon |
| | | | 0.8717 | | | AIR |
| 3F | 3.3350 CX | 0.7598 CC | 0.3750 | 2.1600 | 1.3600 | E48R Zeon |
| | | | 1.0050 | | | AIR |
| 4F | 1.1403 CX | −1.8231 CX | 0.5000 | 1.0400 | 0.8400 | E48R Zeon |
| | | | 0.1919 | | | AIR |
| SF(STOP) | INF | | 0.1550 | | 0.4384 | (STOP) |

TABLE 1.1.-continued

| | | | | | | |
|---|---|---|---|---|---|---|
| 5F | 12.5245 CX | −0.5000 CX | 0.7500 | 0.6400 | 0.9400 | E48R Zeon |
| 6F | 0.5000 CC | −1.4850 CX | 0.4000 | 0.9400 | 1.3800 | OKP4HT Osaka |
| | IMAGE DISTANCE = | | 1.3764 | | | |
| IMG (Image) | INF | | | | 2.4730 | |

NOTES
Positive radius indicates the center of curvature is to the right
Negative radius indicates the center of curvature is to the left
Dimensions are given in millimeters
Thickness is axial distance to next surface
Image diameter shown above is a paraxial value,
it is not a ray traced value
Other material suppliers can be used if their materials are
functionally equivalent to the extent needed by the design;
contact the designer for approval of substitutions.

APERTURE DATA

| | | DIAMETER | | DECENTER | | |
|---|---|---|---|---|---|---|
| APERTURE | SHAPE | X | Y | X | Y | ROTATION |
| C-1 | RECTANGLE | 3.674 | 2.738 | | | |

REFERENCE WAVELENGTH = 525.0 NM
SPECTRAL REGION = 450.0-600.0 NM (450,487.5, 525, 562.5, 600 NM)

INFINITE CONJUGATES

| | |
|---|---|
| EFL = | 0.9029 |
| BFL = | 1.3530 |
| FFL = | 4.9242 |
| F/NO = | 4.3933 |

AT USED CONJUGATES

| | |
|---|---|
| REDUCTION = | 0.0699 |
| FINITE F/NO = | 4.5000 |
| OBJECT DIST = | 8.0000 |
| TOTAL TRACK = | 17.6440 |
| IMAGE DIST = | 1.3764 |
| OAL = | 8.2676 |
| PARAXIAL | |
| IMAGE HT = | 0.7904 |
| IMAGE DIST = | 1.4161 |
| SEMI-FIELD | |
| ANGLE = | 70.0000 |
| ENTR PUPIL | |
| DIAMETER = | 0.2055 |
| DISTANCE = | 5.2379 |
| EXIT PUPIL | |
| DIAMETER = | 0.5915 |
| DISTANCE = | −1.2456 |

NOTES
FFL is measured from the first surface
BFL is measured from the last surface

TABLE 1.2

| ELEMENT NUMBER | SURFACE DESCRIPTION RADIUS OF CURVATURE | | SEPARATION or THICKNESS | APERTURE DIAMETER | | MATERIAL |
|---|---|---|---|---|---|---|
| | FRONT | BACK | | FRONT | BACK | |
| OBJ (object) | 9.2693 | | 8.0000 | | | AIR |
| 1R | 5.0400 CX | 4.5400 CC | 0.5000 0.7693 | 8.0000 | 8.0000 | ACRYLIC |
| 2R | 2.3326 CX | A(1) | 0.2500 0.6349 | 2.5800 | 1.4400 | E48R Zeon |

TABLE 1.2-continued

| | | | | | | |
|---|---|---|---|---|---|---|
| 3R | 1.3966 CX | 12.6000 CC | 0.5000 | 1.3600 | 1.0600 | OKP4HT Osaka |
| | | | 0.4088 | | | |
| SR(stop) | | | APERTURE STOP | 0.3437 | | |
| | | | | 0.1000 | | |
| 4R | 3.1930 CX | A(2) | 0.5871 | 0.5800 | 1.0000 | E48R Zeon |
| | | Image Distance = 1.5192 | | | | |
| IMG (image) | INF | | | 2.4646 | | |

NOTES  Positive radius indicates the center of curvature is to the right
Negative radius indicates the center of curvature is to the left
Dimensions are given in millimeters
Thickness is axial distance to next surface
Image diameter shown above is a paraxial value, it is not a ray traced value
Other material suppliers can be used if their materials are functionally equivalent to the extent needed by the design;
contact the designer for approval of substitutions.

APERTURE DATA

| | | DIAMETER | | DECENTER | | |
|---|---|---|---|---|---|---|
| APERTURE | SHAPE | X | Y | X | Y | ROTATION |
| C-1 | RECTANGLE | 3.674 | 2.738 | | | |

ASPHERIC CONSTANTS $$Z = \frac{(CURV)Y^2}{1 + \left(1 - (1+K)(CURV)^2 Y^2\right)^{1/2}} + (A)Y^4 + (B)Y^6 + (C)Y^8 + (D)Y^{10}$$

| ASPHERIC | CURV | K | A | B | C | D |
|---|---|---|---|---|---|---|
| A(1) | 1.88334282 | −0.51809943 | | | | |
| A(2) | −1.17042980 | −1.71474323 | | | | |

REFERENCE WAVELENGTH = 525.0 NM
SPECTRAL REGION = 450.0-600.0 NM (450, 487.5, 525, 562.5, 600 NM)

INFINITE CONJUGATES

EFL = 0.9854
BFL = 1.4472
FFL = 1.7175
F/NO = 4.2992
AT USED CONJUGATES

REDUCTION = 0.1014
FINITE F/NO = 4.5000
OBJECT DIST = 8.0000
TOTAL TRACK = 13.2693
IMAGE DIST = 1.5192
OAL = 3.7501
PARAXIAL

IMAGE HT = 0.7773
IMAGE DIST = 1.5471
SEMI-FIELD
ANGLE = 50.0000
ENTR PUPIL

DIAMETER = 0.2292
DISTANCE = 2.1708
EXIT PUPIL

DIAMETER = 0.4982
DISTANCE = −0.6949

NOTES  FFL is measured from the first surface
BFL is measured from the last surface Such a consideration, accepted in related art, at least in part is explained by the specifics of the practical use of the system, where user generally positions the optical system such that the object of interest is in the center of the field. Based on the satisfying performance demonstrated by the MTF curves of FIG. 9, the proposed design is operationally sound at least in the visible portion of the optical spectrum.

Non-Limiting Example of a Rear (or Lateral) Optical Imaging System.

Figure 10:
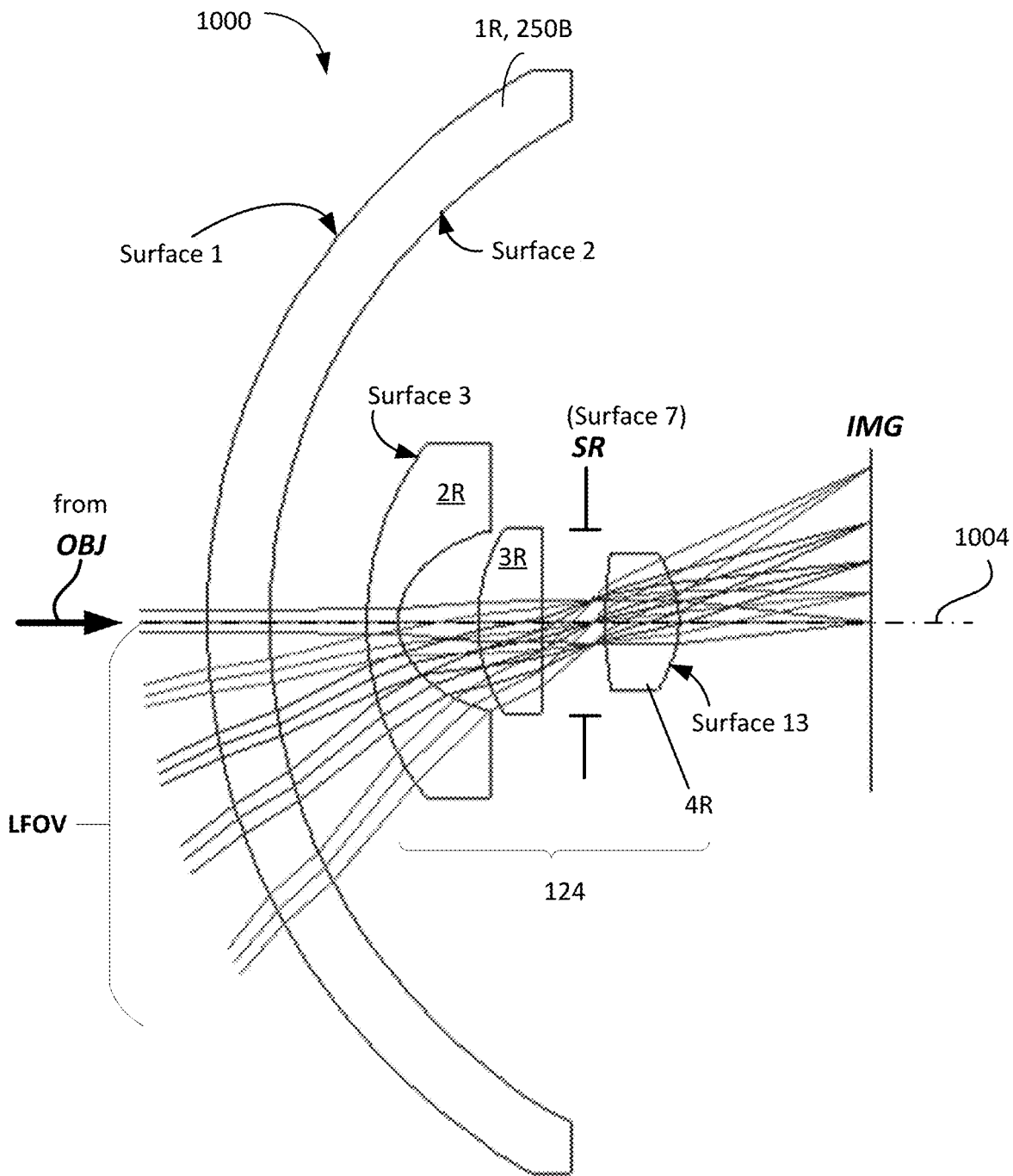
FIG. 10 provides a schematic of an optical train of a lens configured to image a portion of the object space covered by the LFOV (such as lens 124 of an embodiment of FIGS. 1, 2) of the imaging system of an embodiment of the invention.

Table 1.2 as well as FIG. 10 provide description of an embodiment 1000 of the rear optical imaging system (also referred to as a lateral optical imaging system) that is characterized by an f-number of about f/4.5 and includes the optical train defined by the lens element 250B provided by the shell/housing of the optoelectronic system 200 in combination with the rear lens 124. Here, the numbering of the individual optical elements and optical surfaces is specific to FIG. 10 only. Not all surfaces of all of the lens elements are expressly indicated. Light within the range of viewing angles of the system 1000 that corresponds to the LFOV arrives along the local optical axis 1004 at the front surface of the lens element 1R (specifically, at surface 1 of the design, see Table 1.2) that is configured to transmit this light through the lens element 1R with the axial thickness of about 0.5 mm, through the surface 2, and towards the lens element 2R (which is bound by the surfaces 3 and 4, respectively). Upon sequentially traversing the lens element 3R, the light from the LFOV arrives at the surface corresponding to the aperture stop SR (which is surface 7 of the current embodiment, separated by about 0.41 mm from the lens element 3R and by about 0.1 mm from the lens element 4R). Having passed through the aperture stop SR, light from the LFOV traverses the lens element 4R and then impinges onto the optical detector of the sub-system 120, on the sensing surface of which it forms an image IMG the portion of the object space covered by the LFOV.

A person of skill will readily appreciate that, since the operations requirements on the quality of imaging produced by the lateral optical imaging system are more loose than those on the performance of the lens 600 operating in the FFOV, and since the LFOV is not as wide as the FFOV, smaller degree of corrections of aberrations may be sufficient. As a result, the lateral lens 1000 can be made operationally practical with the use of only one meniscus lens element 2R after the incident light passes through the portion of the shell dome 250B, 1R. The positive lens elements 3R, 4R introduce corrections of the aberrations present after the lens element 2R, while the correction of color aberrations can be omitted (in comparison with the lens 600).

Here, the same conventions are assumed for signed of radii and curvatures, dimensions, labeling of aspheric surfaces and other geometrical considerations as those already alluded to above.

As shown in the specific example of FIG. 10, light arriving to the front surface (as shown—surface 3) of the rear lens 124 from the LFOV passes through the first group of lens elements represented by a sequence of the negative meniscus lens element 2R and a positive lens element 3R. Immediately prior to impinging on the image surface IMG, the same light traverses a second group of lens elements represented by the positive lens element 4R. There is no optical element between the first and second groups of lens elements of the rear lens 124, but only an air-gap. The optically-transparent portion 250B of the housing shell is dimensioned as yet another negative meniscus 1R.

Figure 11:
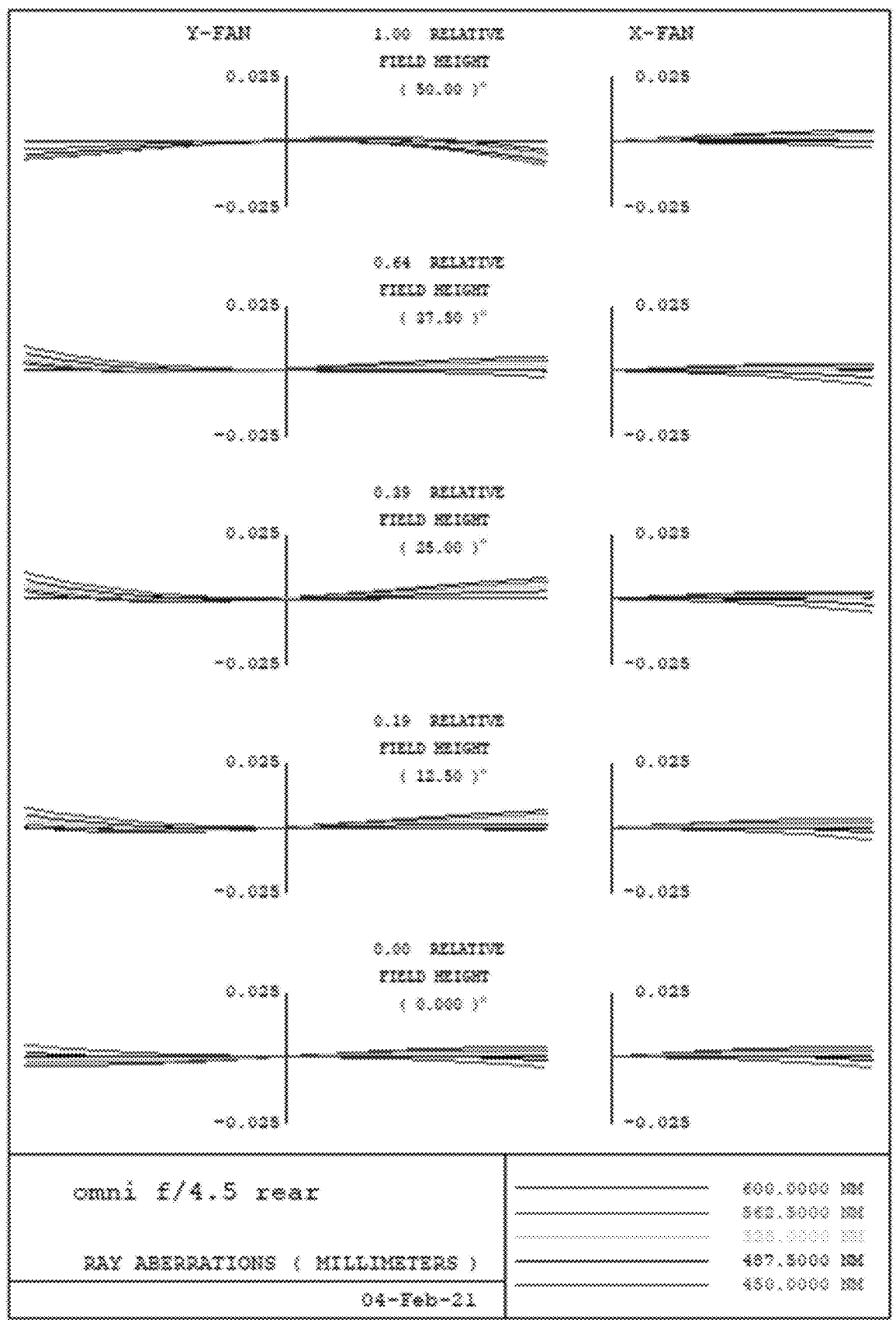
FIG. 11 provides description of transverse ray aberrations during the optical imaging in the LFOV through the lens of FIG. 10.
Figure 12A:
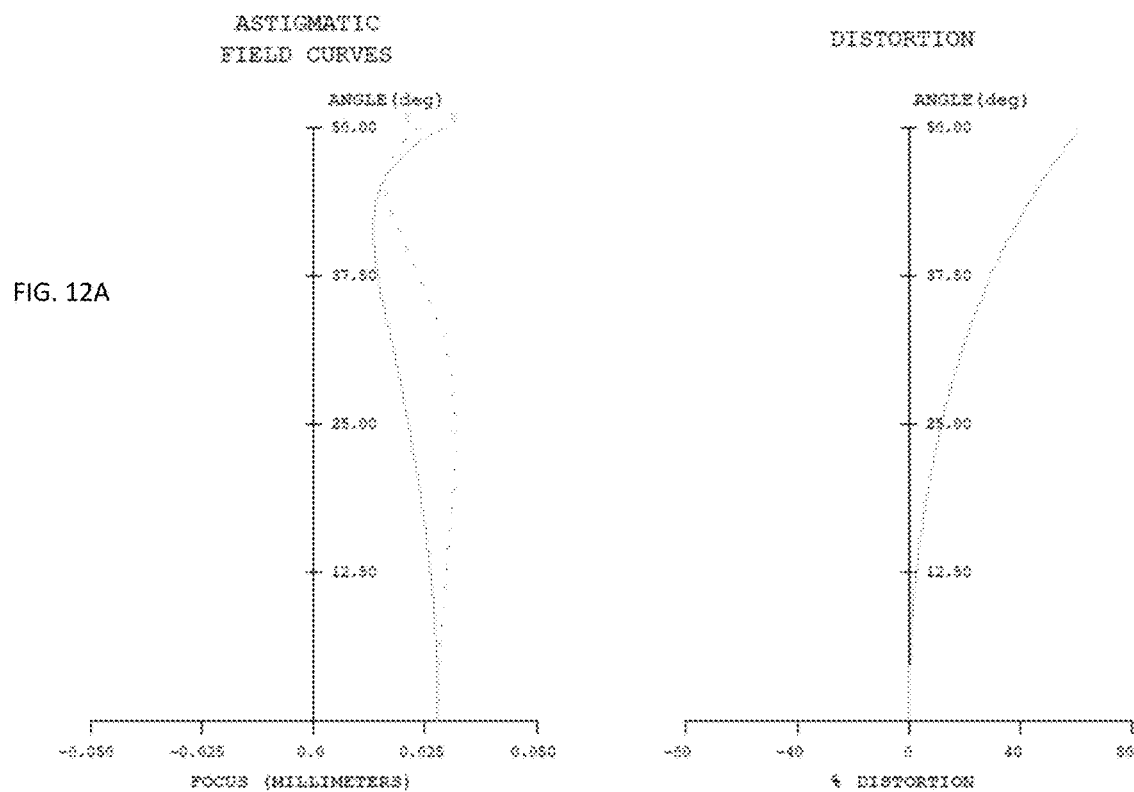
FIGS. 12A, 12B illustrate field curves, distortion characteristics, and the spot diagrams associated with the practical use of the embodiment of FIG. 10 during imaging of the object space in the LFOV only
Figure 12B:
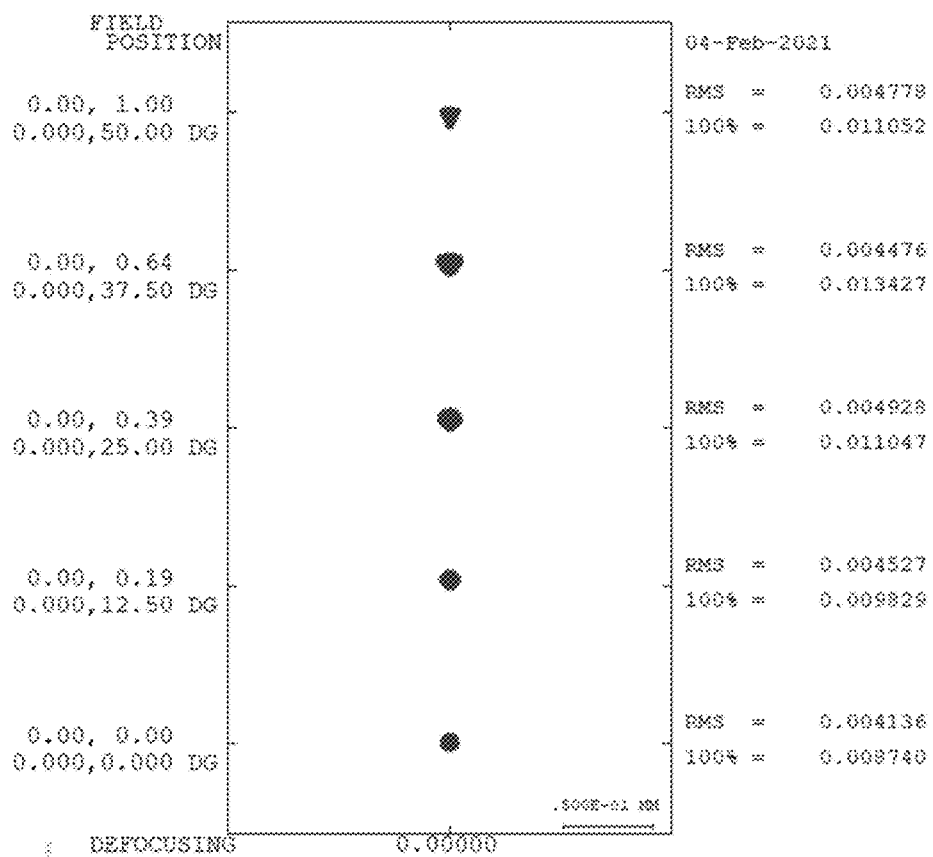

FIG. 11 illustrates transverse ray aberrations representing optical performance of the embodiment 600 during the imaging of the object space in the LFOV: these aberrations are substantially below 12 microns for any field up to 70 degrees (which represents the relative field height of unity) for light at any of wavelengths of 450 nm, 487.5 nm, 525 nm, 562.5 nm, and 600 nm. FIG. 12A illustrates the corresponding field curvature and distortion characteristics as a function of field angle. The distortion figure, for example, is notably within only 5% for field angles up to about 12 degrees, and within less than 15% for field angles up to about 25 degrees. The spot diagrams, illustrated in FIG. 12B, demonstrate the rms spot size below 4.8 microns for imaging at the full field height (field of 70 degrees) and of about 4.1 microns form imaging the axial portion of the object in the LFOV.

Figure 13:
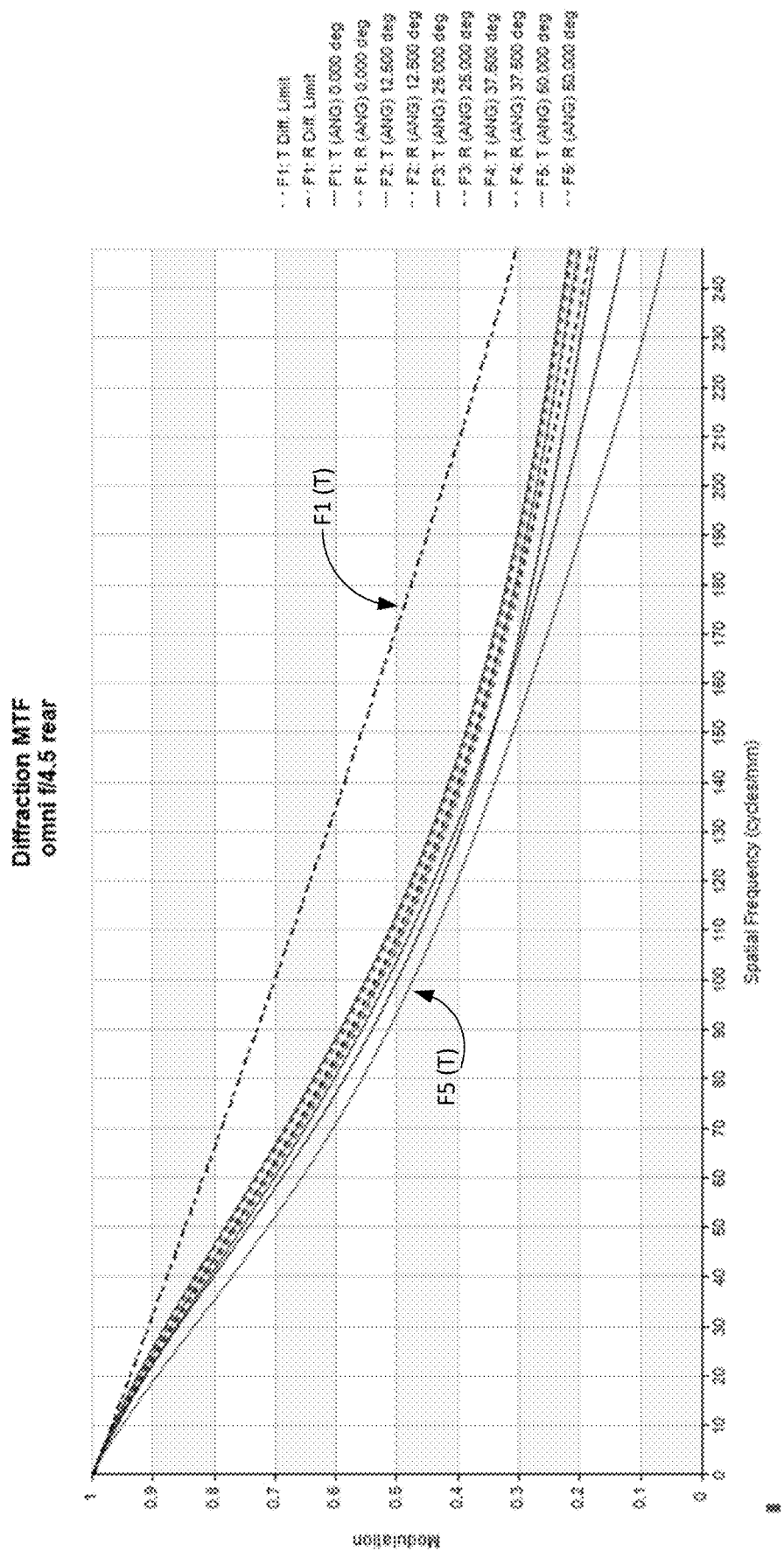
FIG. 13 presents the curves of the modulated transfer function (versus field) for the embodiment of FIG. 6 that characterizes the optical imaging in the LFOV only.

For assessing other types of aberrations, the identification of what is practically acceptable comes down to the modulated transfer function (MTF) curves. Based on the proposed design and in reference to FIG. 13 (that illustrates parameters of the MTF characterizing the operation of the embodiment 200 in the visible portion of the spectrum in the LFOV), the ideal solution is substantially close to being diffraction-limited (the top curve among the MTF curves). Notably, the performance of the design on-axis is close to the ideal solution, with some falloff at the edge of the field—and would be considered practically acceptable by a person of ordinary skill in the art in visual and/or photographic optical systems. Specifically, the cut-off frequency of operation in the visible portion of the spectrum is always way above 240 cycles/mm (both for imaging in both tangential and sagittal planes) for any field up to the elative field height of unity (corresponding to 70 degrees).

Such a consideration, accepted in related art, at least in part is explained by the specifics of the practical use of the system, where user generally positions the optical system such that the object of interest is in the center of the field. Based on the satisfying performance demonstrated by the MTF curves of FIG. 13, the proposed design is operationally sound at least in the visible portion of the optical spectrum.

Notably, in practice, the lens elements 250A, 250B defined by the optically-transparent portions of the shell should be made with thickness that is substantially constant as a function of angle with respect to the local optical axis—otherwise, the meniscus elements 250A, 250B will be characterized by the optical power that changes as function of angle. The housing shell with the optically-transparent portions 250A, 250B that have constant thickness is within the scope of the present invention.

Creation of Co-Oriented and Co-Directional Images by Transforming an Acquired Optical Image.

An embodiment of the opto-electronic system of the invention—such as, for example, an embodiment 200—generates, in independent imaging operation of the sub-systems 114 and 124—visual representations of the portions of the object space that are covered, respectively, by the FFOV and the LFOV. When and if the optical detector system collecting light acquired through the first and second sub-systems 114, 124 includes only one, single detector, such visual representations are not necessarily co-oriented and co-directional sub-images of the object space. Thereafter, according to the idea of the invention, the produced images have to be appropriately transformed into new images that satisfy these criteria.

Therefore, a problem of visual perception of sub-images that are formed—as not co-oriented and not co-directional portions of the overall, aggregate image—in different fields of view as by a multi-FOV optical system on a single optical detector is solved by transforming the spatial distribution of irradiance in at least one of such sub-images to create different spatial distributions of irradiance that satisfy the co-oriented/co-directional criteria. According to the idea of the invention, this transformation is achieved, at least in part, by rearranging or remapping the spatial distribution of irradiance in and image of the LFOV with respect to the identified reference circle of a pre-defined radius. The use of this embodiment of the invention enables the use to transform the not co-direction and/or not co-oriented sub-images of the FFOV and LFOV, generated with the use of a conventionally-structured system, into the sub-images that are co-oriented and co-directional.

Figure 15:
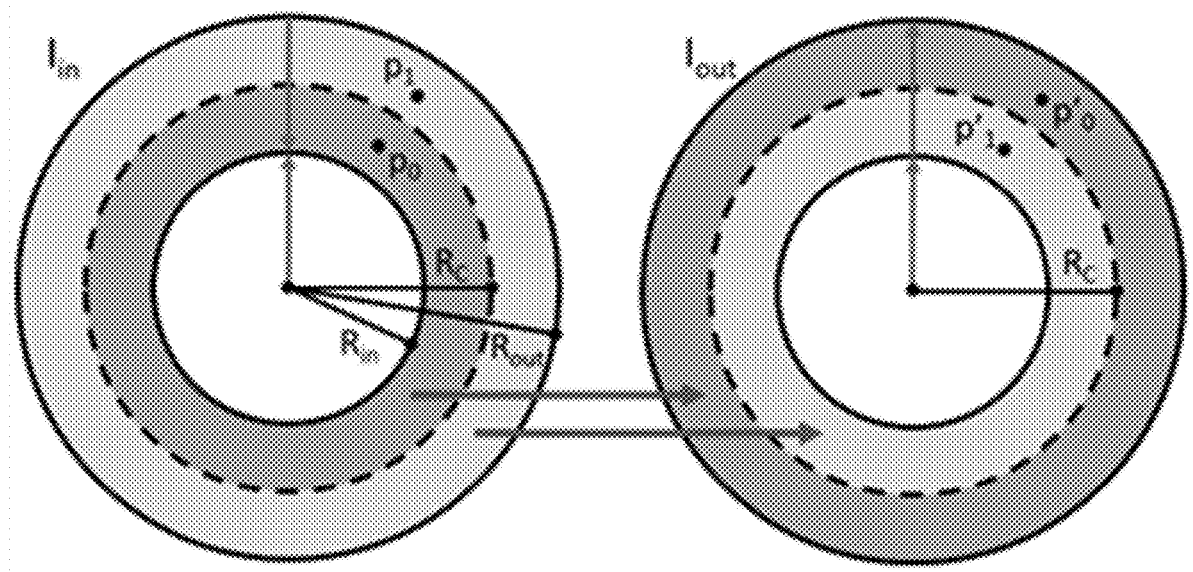
FIG. 15 provides an illustration to various definitions used in the image re-mapping process configured according to the idea of the invention. Here, shaded areas are remapped from $I_{in}$ to $I_{out}$.

The idea behind the targeted spatial redistribution of irradiance of the initially not-co-directional images is based on reflecting upon itself the sub-image representing the object space in the LFOV across a circle with a chosen radius $R_C$. In reference to the schematic of FIG. 15, the LFOV image is in the area (portion of the aggregate image) defined in the image plane between the radius $R_{in}$ (providing a "seam" between the LFOV and FFOV views in the image plane) and the radius $R_{out}$, which is the outer limit of the LFOV view. $R_C$ is judiciously selected based on $R_{in}$ and $R_{out}$, in a form containing and arithmetic mean and/or geometric mean of $R_{in}$ and $R_{out}$.

$$R_C = \frac{R_{in} + R_{out}}{2} \tag{1}$$

$$R_C = \sqrt{R_{in} R_{out}} \tag{2}$$

In the spatially-continuous domain, the image transformation can be defined by a remapping function $f(r)$ configured to transform the value of the radius $r_0$ of a point $p_0=(r_0; \theta)$ in the LFOV portion of the image by reflecting the point $p_0$ across $R_C$ to define point $p_1$ with the radius $r_1: p_1=(r_1; \theta)$. Notably, the remapping does not change the angle $\theta$ of the point's polar coordinate representation. Given these requirements, two limiting remapping functions can be chosen:
the function $f_a(r)$ for the situation when $R_C$ is defined as the arithmetic mean of the rear radii (see Eq 1); or
the function $f_g(r)$ for the situation when $R_C$ is defined as the geometric mean of the rear radii (see Eq 2).

$$f_a(r) = 2R_C - r \tag{3}$$

$$f_g(r) = R_C^2 / r \tag{4}$$

As intended, for each of these functions $f_a$, $f_9$ no remapping of the irradiance distribution of the image occurs when $r = R_C$:

$$f(R_C) = R_C \tag{5}$$

Considering the fact that a given image formed by the optical system is represented by a pixelated distribution of optical radiation (due to the pixelated nature of a typical optical detector receiving the light delivered by the optical imaging system), an embodiment of the image-transformation procedure of the invention provides the methodology of conversion of irradiance distribution between the spatially-discrete and spatially-continuous domains.

The transformation of the discrete domain to the continuous domain is performed as follows. In further reference to FIG. 15—the input image portion $I_{in}$ and the output image portion $I_{out}$ are each represented by two-dimensional arrays of pixels, with number of rows and columns $n_{row}$ and $n_{col}$. A pixel P has a row and column $(P_{col}, P_{row})$. Each pixel P in either of these images can be converted into a point p in the continuous domain with the following equation:

$$p=(x_p, y_p)=(P_{col}-n_{col}/2+\tfrac{1}{2}, P_{row}-n_{row}/2+\tfrac{1}{2}) \tag{6}$$

The "½" terms in Eq. 6 perform the task of "moving" the pixel to the center of the square it defines. Regardless of which of major colors (R, G, B) a given pixel represents, such square is defined as having a side length of 1, which identifies the coordinates $(P_{col}, P_{row})$ with the upper left corner of the square associated with P. (Here, the direction of the y-axis is defined a pointing down, which is a standard notation in image representation in software). Adding ½ makes the point associated with this pixel in the center of the pixel's square. Additionally, t half the number of columns/rows is subtracted to move the origin of the point to the center of the image. As a result, the use of polar coordinates of the points can be made as their center shares the center of radii $R_C$, $R_{in}$, and $R_{out}$.

Once a given pixel of an image is converted to spatially-continuous domain, the polar coordinates of the point p, $(r_p, \theta_p)$, are found. Then, point $p'=(f(r_p), \theta)$ is defined, which is point p remapped in the continuous domain as discussed above. Using the so-defined image point p', color values P of this image point are determined with the use of interpolation procedure. The interpolation procedure involves first converting p' to a point $p_I'$ in the discrete image domain by using the inverted form of Eq 6:

$$p_I'=(x_{p'}, y_{p'})=(x_p+n_{col}/2-\tfrac{1}{2}, y_p+n_{row}/2-\tfrac{1}{2}) \tag{7}$$

Interpolation takes the point $p'_I$ on the image and selects color values for it based on that image based on, for example, linear interpolation between nearest neighbors.

Irradiance-redistribution may be carried out starting with the output pixels of the acquired image, due to the reflective nature of the remapping functions that provide unique one-to-one correspondence between the pixels of the initial and transformed images regardless of whether the arithmetic or geometric remapping function is chosen $f(r_0)=r_1 \Rightarrow f(r_1) = r_0$. For an output (transformed) image $I_{out}$ of the object space seen in the LFOV, each pixel P in the image with an associated continuous domain point p in the rear view is assigned color and/or irradiance values by finding $p'_I$ associated with p, then irradiance values are interpolated from the input (initial) image $I_{in}$. For pixels with p that are not present in the LFOV, the color/irradiance values associated with the pixel are simply copied from the corresponding pixels having the same spatial coordinates in the initial image $I_{in}$. The $p'_I$ associated with each pixel P can be calculated once each time $R_{in}$ or $R_{out}$ is redefined and later use as reference data.

Figure 16A:
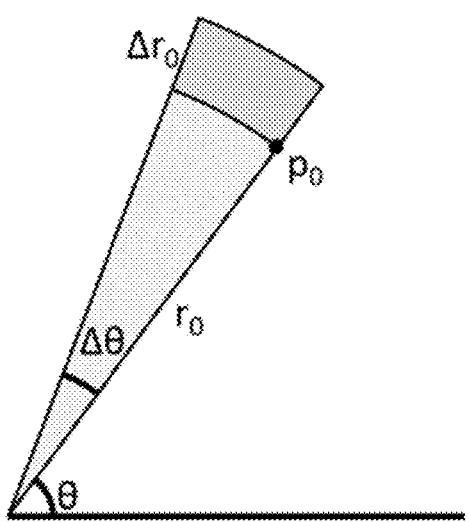
FIGS. 16A, 16B schematically illustrate shapes used to define Aspect Ratio Preservation during the geometric mapping of the points of the conventional (not co-oriented and not co-directional) images formed with the use of a conventional optical imaging system to the points of the re-mapped (co-directional and co-oriented) images.
Figure 16B:
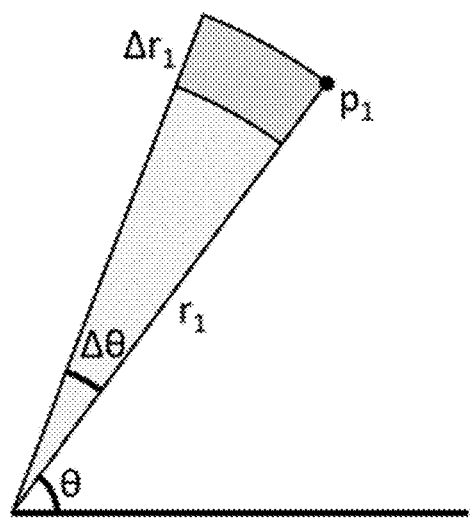

A person of skill in the art will readily appreciate that re-distribution of irradiance used to transform the optically-acquired image to change its directionality requires preserving the aspect ratio of a given pixel of the image upon such transformation 9 as the radial coordinate of the pixel if being changed). FIGS. 16A, 16B schematically illustrate spatial geometrical parameters used to define Aspect Ratio Preservation during the geometric mapping of the points of the conventional (not co-oriented and not co-directional) images formed with the use of a conventional optical imaging system to the points of the re-mapped (co-directional and co-oriented) images.

As mentioned above, when selecting a particular remapping function, one can choose $f_a(r)$ of (Eq 3) to ensure the radius of reflection $R_C$ is halfway between $R_{in}$ and $R_{out}$. Or one can choose $f_g(r)$ of (Eq 4), to maintain the aspect ratio of dimensions of corresponding pixels of the initial image and the transformed image. In a related embodiment, a remapping function can combine both $f_a(r)$ and $f_g(r)$ with appropriate weights.

For a given point $p_0=(r_0, \theta)$ in the LFOV view, the first shape is defined as the space bounded between the radii of $r_0$ to $r_0+\Delta r_0$ and the angular sector from $\theta$ to $\theta+\Delta\theta$. See FIG. 16A. Similarly, for a transformed point $p_1=(f(r_0), \theta)$, the second shape is defined by the space bound between radii $r_1$ and $r_1 - \Delta r_1$ and the angular sector $\theta$ to $\theta+\Delta\theta$. See FIG. 16B. (Note that $\Delta r_1$ is subtracted due to the reflection of the image, which inverts the sign of $\Delta r_1$). Two ratios relating these first and second shapes are: the ratio of heights $H(r_0)$ and the ratio of widths $W(r_0)$, as defined in Eqs. (8) and (9), written for small angle approximations to convert circle section length to chord length and by letting $\Delta r_0$ approach zero.

$$H(r_0) = {}^{-\Delta r}{}_1/\Delta r_0 = df(r_0)/dr_0 = -f'(r_0) \tag{8}$$

$$W(r_0) = r_1 \Delta\theta / r_0 \Delta\theta = f(r_0)/r_0 \tag{9}$$

To prevent image distortion, $H(r)$ and $W(r)$ are chosen to be defined in the same fashion, so that any increase in height ratio is similarly found in an increase in width ratio. Setting these two equal preserves the aspect ratio through the reflection.

$$H(r) = W(r) \text{ and } -f'(r) = f(r)/f \tag{10}$$

It can be seen that $f_g(r)$ from Eq 4 is a solution to the differential equation Eq 10, which means it will preserve aspect ratio.

Weighting Functions

Figure 17:
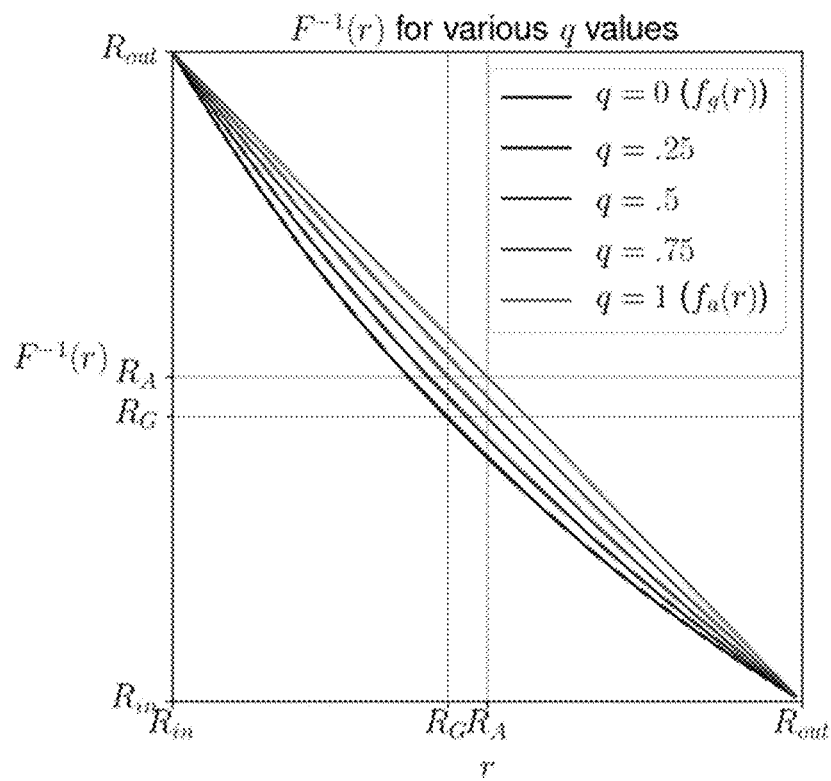
FIG. 17 contains plots illustrating inverse mapping for various values of the input parameter q.

The use of arithmetic and geometric remapping functions, $f_a(r)$ and $f_g(r)$, for spatial redistribution of the image irradiance may have very different effects on usability of an output (transformed) image. FIG. 17 contains plots illustrating inverse mapping for various values of the input parameter q.

In order to find a compromise between the advantages of either function, a more general remapping function $F(r)$ is formed with an input parameter q, which is a weighting value, where $0 \leq q \leq 1$ and $q' = 1-q$:

$$\begin{cases} F(r) = q f_a(r) + q' f_q(r) \\ R_A = \dfrac{R_{in} + R_{out}}{2} \\ R_G = \sqrt{R_{in} R_{out}} \\ F(r) = q(2R_A - r) + (1-q)R_G^2/r \end{cases} \tag{11}$$

$$F^{-1}(r) = \dfrac{(2qR_A - r) + \sqrt{(2qR_A - r)^2 + 4q'qR_G^2}}{2q} \tag{12}$$

Note that $f_a(r)$ uses $R_C = R_A$ and $f_g(r)$ uses $R_C = R_G$. $F(r)$ is not reflective like $f_a(r)$ and $f_g(r)$ so one has to find its inverse, $F^{-1}(r)$.

When using this inverse mapping, the user finds the input point associated with each output pixel. When q=0, $F(r) = f_g(r)$, and when q=1, $F(r) = f_a(r)$. Therefore, the weighting value of q can be changed, depending on the specific implementation of the irradiance-redistribution, between 0 and 1 to define a remapping function $F(r)$ that works as a compromise between the arithmetic mean and geometric mean remapping functions.

The methodology of redistribution of irradiance of an image portion representing the object space observed in the LFOV with the purpose of forming a transformed image portion with reversed directionality can be summarized as follows:

1) Start with a blank output (transformed) image. The output (transformed) image is built one pixel at a time.
2) To determine the value for each pixel p in the output image:
a. Use p's column and row, $(p_{col}, p_{row})$, to find the pixel's position relative to the center of the output image: $(x_{out}, y_{out})$.
b. Convert this position to polar coordinates: $(r_{out}, \theta_{out})$.
c. Find the remapping source position for this pixel: $(r_{in}, \theta_{in}) = (f(r_{out}), \theta_{out})$.
d. Convert the source position to Cartesian coordinates relative to the origin of the image (origin is the top-left corner): $(x_{in}, y_{in})$.
e. Use bilinear interpolation to obtain a color value of the input image using the source position coordinates.
f. This takes a continuous position on an image, $(x_{in}, y_{in})$ {e.g. the position (4.326, 2.195)} and finds the value it should be using a weighted average of the discrete pixels it is nearest to, {e.g. the pixels at coordinates (4,2), (4,3), (5,2), (5,3)}.
3) Set the value of each output image pixel using the above method. The values of pixels which aren't within the remapping range are simply copied from the input image (these pixels make up the front view).

Additionally, the following steps can be taken during the spatial re-distribution of the irradiance of the initial image to reduce redundancy of the procedure:

Upon any change to calibration settings that modify the remapping, construct a data structure M that maps a pixel p on the output image to a position on the input image using steps 2a-2d above: $M[p_{col}, p_{row}] = (x_{in}, y_{in})$.
Replace steps 2a-2d in the above process with the following:
Find $(x_{in}, y_{in})$ for p, by obtaining the position on the input image from the data structure: $M[p_{col}, p_{row}] = (x_{in}, y_{in})$.

Having advantage of understanding this methodology, a skilled person will now readily appreciate that the scope of the invention includes a method for forming an image of an object space with the use of an optoelectronic system, as well as a computer-program product for transforming first and second individual images formed in light acquired from an object space by an optical imaging system in a FFOV and an LFOV of the optical imaging system, respectively, into images that are co-directional. Such computer-program product includes a computer-usable tangible non-transitory storage medium having computer-readable program code thereon, and the computer-readable program code includes program code for effectuating specified processing steps that include: (a) transforming one of the first and second individual images into a third individual image by radially changing a distribution of irradiance of the first image with respect to a circumference of a circle of a chosen radius located within an outer perimeter of said one of the first and second individual images and assigning a radially-changed distribution of irradiance of the first image to the third image (here, the third image has a directionality equal to a directionality of a remaining of the first and second individual image), and (b) generating a report containing a visually-perceivable representation of at least one of the first individual image, the second individual image, and the third individual image. Alternatively or in addition, the program code may be structured to carry out formatting one of the remaining of the first and second individual images and the third image as a stripe or band having an inner perimeter that is a circumference of an inner circle and an outer perimeter that is a circumference of an outer circle (with a radius of the inner circle being no smaller than an outer radius of the one of the first and second individual images and a radius of the outer circle is larger than the radius of the inner circle), and/or dimensioning the one of the remaining of the first and second individual images and the third image as an annulus having an inner perimeter and an outer perimeter (the inner perimeter being a circle with an inner diameter that is no smaller than an outer radius of the one of the first and second individual images, and the outer perimeter being a circle of with an outer diameter that is larger than the inner diameter). In the latter case, for example, the step of generating may include forming the visually-perceivable representation that contains the one of the remaining of the first and second individual images and the third image to be radially separated by a gap (with no point in the gap optically corresponding to any of a first portion of the object space covered by the FFOV and a second portion of the object space covered by the LFOV).

Images of the Identified Indicia Formed with the Imaging System of Example 1.

It is understood, therefore, that in stark contradistinction with the operation of the imaging system of related art, embodiments of the present invention are configured to form different aggregate image of the object space, in which sub-images corresponding to the FFOV and the LFOV are both co-oriented and co-directional.

Figure 18A:
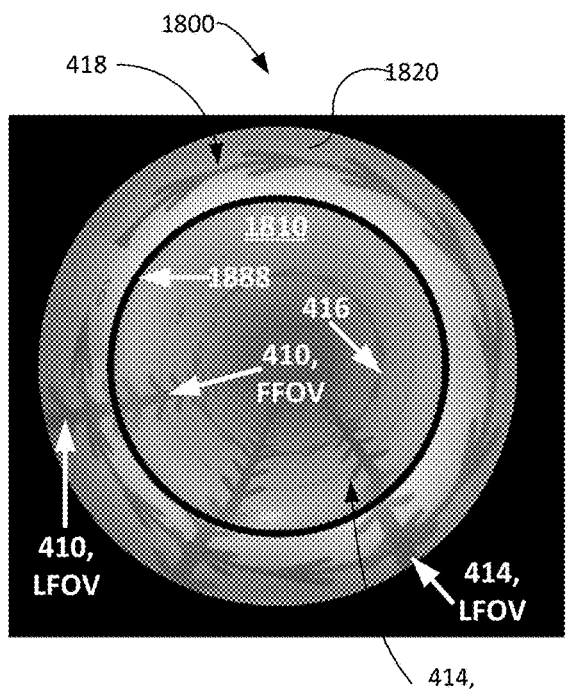
FIGS. 18A, 18B are images of a (tubular) object space marked with indicia of FIGS. 4A, 4B from the inside and formed with an embodiment of an imaging system configured according to the idea of the invention.
Figure 18B:
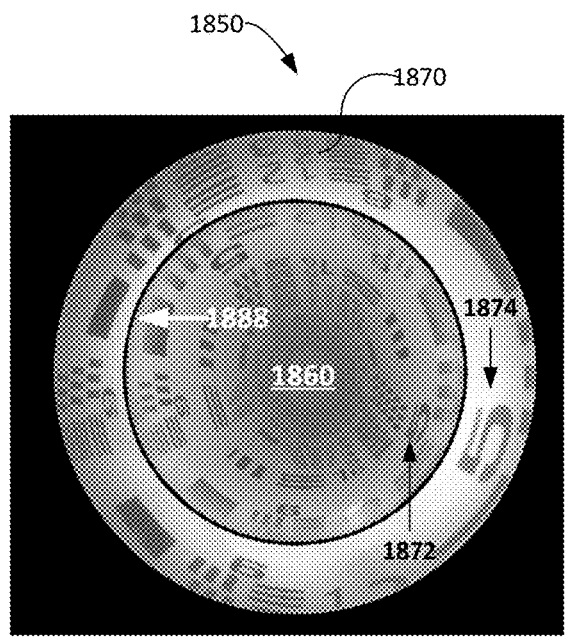

FIGS. 18A, 18B illustrate aggregate images 1800, 1850, formed by imaging the chosen (tubularly shaped) object space (marked with, respectively, indicia 400 and 450) with the embodiment 200 discussed in reference to FIGS. 6-13 and Tables 1.1, 1.2 and transformed according to the above-discussed image-irradiance redistribution methodology.

The central portions 1810, 1860 of the images 1800, 1850 represent the portions of the object space viewed by the system 200 in its corresponding FFOV, while the annular portions 1820, 1870 of the images 1800, 1850 represent the portions of the object space imaged by the system 200 in its corresponding LFOV and then appropriately transformed utilizing the irradiance-redistribution methodology discussed above.

Specifically, and in reference to FIG. 18A, the aggregate visually-perceivable representation 1800 of the object space includes two image portions or sub-images 1810 (representing the imaging of the target 400 covered by the FFOV of the optical portion 116 of the system 200) and 1820 (representing the imaging of the target 400 covered by the LFOV of the optical portion 124 of the system 200). At the chosen position of the imaging system 200 within the tubular member carrying the identified indicia on its inner cylindrical surface, the arrow 416 and the digits 9, 10 of the indicia are seen by the optical systems 116, 124 only in the FFOV, and therefore are shown to be imaged only into the central image portion 1810. The arrow 418 and the digit 6, on the other hand, are viewed by the optical systems 116, 124 only in the LFOV and, therefore, are imaged only into the image portion surrounding the image portion 1810 and then transformed via the spatial distribution of irradiance as discussed, to form the image portion 1820. Arrows 410, 412, 414 that extend along the axis of the tubular member are observed in both FFOV and LFOV and, therefore are imaged into both image portions 1810 and 1820.

A person of skill will easily recognize that the orientations of the final representation of the image portions 1810, 1820 are exactly the same (as seen by the orientations of the digit 6, arrows 410, 414 in the LFOV-based image portion 1820 in comparison with those in the FFOV-based image portion 1810). Additionally, the skilled artisan will immediately understand and appreciate that the directionalities of the image portions 1810, 1820 are also the same.

Similarly, and referring now to FIG. 18B, the aggregate image 1850 of the object space marked with the pre-defined indicia 450, formed with the embodiment 200, includes two image portions 1860 and 1870. These are the images of the object space in the FFOV and LFOV, respectively. The equal orientations of these image portions can be clearly identified by comparing spatial orientations of the elements 1872, 1874 of the indicia (both of which are represented, for example, by a digit 5). A person of skill will immediately recognize that the directionalities of the image portions 1860, 1870 are also the same.

Example 2 of an Optical System Used with an Embodiment of the Invention

Another example of the optical imaging system judiciously structured to be used with an embodiment of the invention was discussed in detail in U.S. patent application Ser. No. 17/087,934, in reference to FIGS. 20A, 20B, 21, 22, 23A, 23B, 24 and Table 2.3 of that application, and, since the disclosure of Ser. No. 17/087,934 is incorporated by reference in the current application, the details of such example will not be reiterated herein to simplify the current disclosure.

Additional Considerations for Implementing an Embodiment of the Invention.

Depending on the environment, a given MVID can be further modified to operate in physical/chemical/biological environments, such as heat/cold, water or fluids, presence of corrosive substances and electro-magnetic interference, as well as regulatory requirements.

For example, the MVID can be configured as an independent imaging device for independent imaging and image recording, using the device or person it is attached to for navigation and positioning; alternatively, it can allow the operator to use the imaging from either of both devices. It can be used to capture still or video images in different formats, including: spectral, multi-spectral, hyper-spectral, absorption, grey-scale, inverted color and binary images, as well as infra-red images.

As discussed, a multi-view imaging device (MVID) or system of the invention may include a single image sensor (such as a Charge Coupled Device, or CCD or a Complementary Metal-Oxide-Semiconductor, or CMOS) or multiple sensors or cameras, to capture multiple views of the object space. The MVID includes an embodiment of the optical imaging system (as discussed elsewhere in this application), and corresponding mechanical housing or casing complemented with or without external or internal illumination sources.

The formed images of the FFOV and LFOV can be configured to be separated in space from one another or be contiguous, but the spatial relationship between different fields of view generally remains unchanged when the corresponding images are captured with a single image sensor. Moreover, any radial gaps between spatially-separated images of different fields of view can be compensated for by the forward or backward movements of the imaging system along the optical axis, thereby allowing for a complete, aggregate image to be obtained with discontinuous views.

To differentiate between the sub-images of the object space seen in the FFOV and in the LFOV formed on a single optical detector of the optical detector system, a slight radial gap can be introduced during the formation of the aggregate visually-perceivable representation of the object space and displayed between these sub-images to help inform the viewer of the distinction between the two (example of such radial gap is shown in FIGS. 7A, 7B, for example, as dark annular bands 788). As an option, an embodiment of the imaging system can also be rotated, in operation, about a longitudinal axis with the use of the attached tether to augment views and to see the sides of tunnels or organs at sharp turns or branches (as in a T or Y junction of pipes or branches of airways in the lungs).

Geometry of a given implementation of the lens system can be varied to provide specific angular ranges of viewing angles in different fields of view as required by a particular application. Depending on the specifics of implementation, the forward viewing angle can be ±90° or smaller, and the rear viewing angle from can be from ±90 to +/−180° or smaller.

As another example, when inspecting the inner walls of a typical industrial pipe, the forward view range of viewing angles (e.g. ±30°) would be used primarily for navigation of the imaging probe, while a lateral view within the range of ±90-150° would provide the required image from the surface of the pipe to show any cracks, debris, or other structural defects.

In yet another example, the range of forward viewing angles can be chosen to be large for inspecting a room or container through a small opening, or the top or base of the human bladder through the urethra. Such an optical system may be configured to possess a FFOV corresponding to the range of viewing angles of ±60°, and an LFOV corresponding to the range of viewing angles ±150-180°. In a related embodiment that may find its use in, e.g., robotic surgery, a substantially 3-dimensional or stereoscopic view of the object space acquired in the FFOV with an imaging probe that contains two optical imaging systems can be combined with a view in an LFOV within the range of viewing angles of, e.g. ±140-180° to allow a clinical specialist (a surgeon, for instance) who is usually located remotely to see instruments and devices that are being introduced to a biological tissue by an assistant, and to insure that small cuts and perforations to the intestines, bladder, blood vessels and nerves are avoided during the instrument entry. The view obtained in the LFOV can be displayed around and surrounding the view representing the FFOV when instruments are being introduced and eliminated (e.g., electronically), thereby allowing the surgeon to concentrate on the forward view alone.

Yet another related embodiment could offer the formation and/or visualization of an image in the LFOV only, in isolation, by itself (without including the forward view), within a range of viewing angles of e.g., ±(90°-150°).

Assembled System: The capsular housing shell encapsulates the lenses, CMOS sensors, LEDs, rigid flex PCB, with a slightly smaller cylindrical diameters at the front and rear than at the center (FIG. 1). As an example, a capsule that is about 10-13 mm in diameter with a length of about 20-25 mm to be comparable in size with a typical large medical pill to be swallowed. The material of the capsular housing is made resistant to bodily fluids and/or cleaning solutions, and the dimensions of the capsule facilitate the separation and prevention of collapse of mucosa during the use operation of the embodiment.

Figure 19:
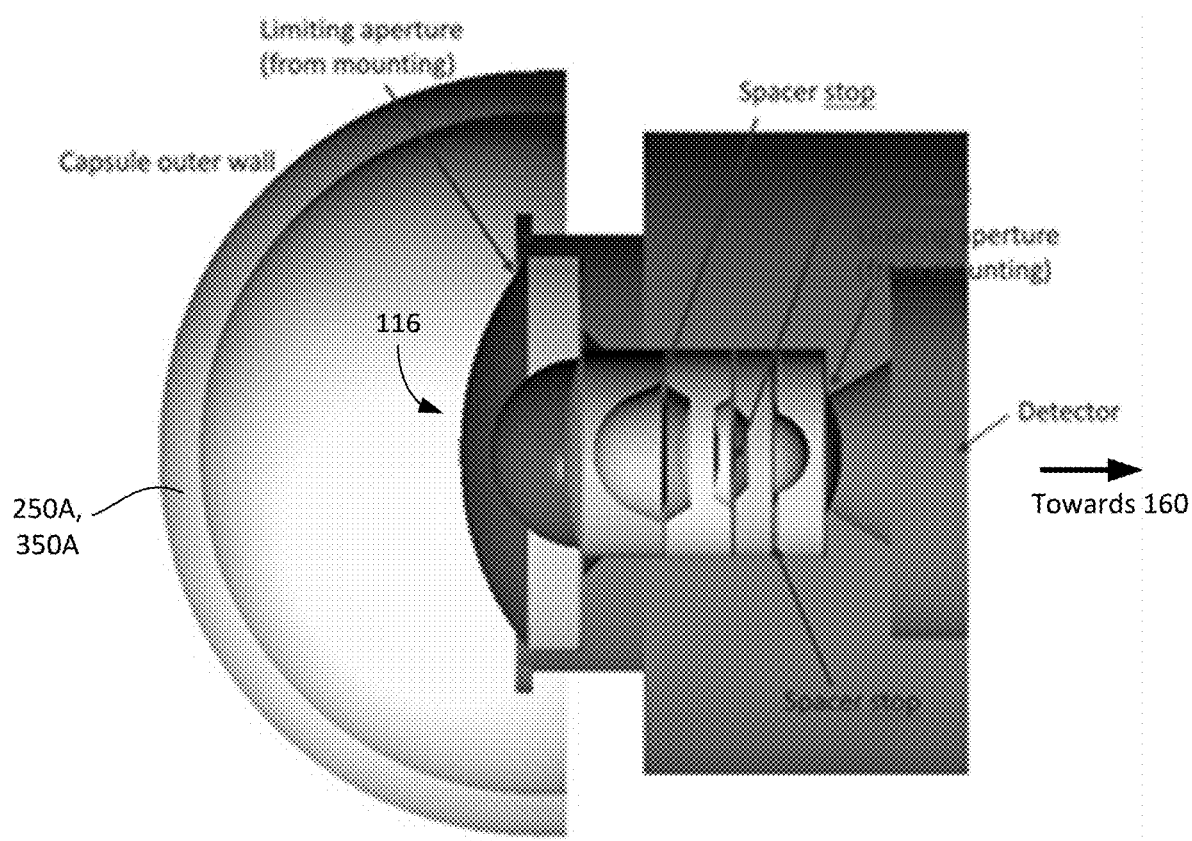
FIG. 19 is a schematic of housing/mounts used for assembly of a front optical imaging system of an embodiment of the invention.

Housing/Mounts: Generally—and in reference to both the front and rear optical imaging systems of an embodiment of the invention—the lens elements are mounted or housed in aluminum-alloy lens-holders with appropriate apertures and spacers judiciously dimensioned to block stray light, as would be understood by a skilled artisan. (In a related implementation, such mounts/holders can be formatted from plastic or other appropriate materials. See for example a schematic of FIG. 19. The image sensors/detectors, each of which uniquely corresponds to and operates with either the front or the rear optical system of an embodiment, are mounted on the corresponding PCBs and attached to the base of the corresponding lens holders. The LEDs that provide the fluxes of the object-space-illuminating light from the front and rear lenses 116, 124 through the lens elements 250A, 250B are mounted at the top of the corresponding lens holders.

Tether: An embodiment of the tether (such as 254 of embodiment 200, or a tether of embodiment 100, which is not shown in Figures) contains individualized shielding around each twisted pair of wires, and is configured to be slim (of about 2-3 mm in outer diameter or narrower) and flexible enough to allow the patient to swallow the capsule and to facilitate passage through the bodily hollows, with the jacket preferably made of polyurethane or silicone. The tether-capsule junction is structured to be water-resistant and have sufficient tensile strength to prevent breakage from pulling or biting.

Movement/position: The tethered capsule with two or more cameras can have several degrees of freedom in a bodily organ to view the organ or cavity in its entirety so as not to miss lesions, such as an ulcer or tumor or vascular lesion in an organ like the stomach, intestine or esophagus and gastroesophageal junction. First degree of freedom is defined by withdrawing or slackening the tether to control the position along the vertical or z-axis. Second degree of freedom is associated with the movement of the patient sideways to change the relative position of the capsule along the transverse or x-axis. Third degree of freedom addresses the movement of the patient forwards and backwards to change the relative position of the capsule along the frontal or y-axis. Forth degree of freedom is manifested in rotation of the tether clockwise or anti-clockwise to 'pan' a full 360 degrees along the latitude or azimuth. This can be accomplished manually or mechanically, or with a powered motor to rotate the tether about its axis.

Transparent hemispheres: The "domes" 250A, 250B, 350A, 350B of the capsular housing (through which light from the object space is delivered to the front and rear lenses 116, 124 of the front and rear optical imaging systems of an embodiment) or even a complete capsular housing (as in the case of embodiment of FIGS. 1A, 1B) may be made of transparent, smooth, water-proof, PMMA (medical grade acrylic). They can also be made of glass or other transparent materials. If and when the capsular housing is configured to include a central segment (such as segments MS1, MS2 or the like, see embodiments 200, 300 for examples) that attaches to the two domes and is sealed to be water-resistant, allowing the entire surface to be cleaned and disinfected using approved cleaning and disinfecting procedures, the central segment may be optionally made to be only partially-transparent or even opaque to light at operational wavelengths. The top or proximal dome is structured to include an opening for the cable and a strain-relief plug 160 (FIGS. 1, 2, 8, 9).

Sensors/Optical detectors: It is preferred that each of the lens assemblies (of which there are two in embodiments 100, 200, 300) has a respectively-corresponding optical detector, one for each lens assembly. The group or combination of such optical detectors, in such case, is preferably disposed to spatially separate the corresponding lenses. Optionally, however, multiple lenses may be served by one optical detector (in which case the images formed in different FOVs of the system are registered in the same physical imaging plane). It is also envisioned, that in a related embodiment (which is not expressly shown in the Figures), e.g., the rear lens 124 may be substituted with a set of multiple rear lenses 124(i), 124(ii), . . . 124(n) that are configured at appropriate angles AA with respect to the axis of the capsular housing around the circumference, for example at regular annular intervals such as to form multiple LFOV optical channels for a given embodiment. Each of such lenses can be complemented by a respectively-corresponding optical detector, or multiple lenses can share the same detector—depending on the specifics of a given embodiment.

The lack of components for wireless transmission and lack of the need for a battery/power source allows a larger image sensor of about 5 mm in diameter to be incorporated in the capsular housing than those used in existing wireless devices. Substantially in any implementation of the idea of the invention, the opto-electronic system in the housing is powered by an external power source via the wire drawn through the corresponding tether. Each optical detector is mounted on a rigid flex printed circuit board (PCB) of up to about 6 mm in size. The rigid-flex PCB contains (6 lanes for three differential-signal pairs, 2 lanes for multiplexer data and clock, and 2 lanes for power and ground). Separate LEDs provide are mounted preferably around the corresponding lens to provide uniform illumination. (Among such illumination sources, there may be both white-light and mono-chromatic LED sources, such as source of blue or cyan-colored light, or sources of other color(s) with wavelengths outside the visible optical spectrum. Monochromatic LEDs allow narrow-band imaging, NBI, to be carried out.)

Electronics: Incorporated in or at a given PCB are at least: a microcontroller, LED drivers, a MIPI CSI-2 multiplexer and a clock generator, to control the power supplies to multiple opto-electronic components, and also to govern the turn on/off, adjustment of brightness, taking snapshots of the object space during or instead of live video imaging capture, using front or rear optical imaging systems simultaneously or independently and/or in time-alternating fashion, with either white light or monochromatic LEDs. By controlling and selectively powering multiple components of a capsule, it is possible to use a thinner tether and minimize heat generation. By including a MIPI multiplexer, microcontroller, voltage regulator, clock generator, and LED driver in the capsule, the number of wires in the cable is reduced to about 10 (from several tens—for example, 30—that are present in cables or catheters of related art).

It is appreciated that the discussed opto-electronic imaging system (imaging probe) generally—and whether or not a specific configuration is expressed in the attached drawings—includes a distal portion in which an opto-electronic circuitry with an embodiment of the optical system of the invention is/are disposed, a proximal portion preferably removably connected to at least a programmable processor and/or an appropriate display device, as well as the housing or sheath (throughout which the optical and/or electrical members operably connecting the programmable processor with the opto-electronic circuitry.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes. Other specific examples of the meaning of the terms "substantially", "about", and/or "approximately" as applied to different practical situations may have been provided elsewhere in this disclosure.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In addition, it is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

The operation of embodiments of the invention, therefore, may require the use of a computer-readable processor/controller the operation of which is governed by specifically coded instructions stored in a tangible, non-transitory storage memory. Such processor is specifically-programmed to perform at least the steps of collecting optical data through the optical system of the imaging probe as described, and processing these data to display the images of the object space scene(s) at an appropriately-chosen display device, thereby transforming the acquired optical data into a tangible visually-perceivable by the use representation of the object space. The memory may be random access memory (RAM), read-only memory (ROM), flash memory or any other memory, or combination thereof, suitable for storing control software or other instructions and data. Instruction information may be conveyed to a processor through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components. Accordingly, a computer-program product encoded in a non-transitory tangible computer readable storage medium and useable with a programmable computer processor to generate portions of images and full images discussed in this disclosure from optical information received by the optical detector (with which the processor is operably cooperated) is also within the scope of the invention. Computer-code implementing all above-discussed image-acquisition and image-transformation steps, and the processor programmed with such computer code are within the scope of the invention as well.

Disclosed aspects, or portions of these aspects, may be combined in ways not listed above. Accordingly, the invention should not be viewed as being limited to the disclosed embodiment(s).

What is claimed is:

1. An optoelectronic system comprising:
   a housing shell having a shell axis and first and second optically-transparent portions of the housing shell that are integrally connected with one another to form a wall of the housing shell that encapsulates and fluidly seals a volume therein, the volume containing:
   an optical detector system,
   a first lens facing a first portion of the housing shell that has a first non-zero optical power, a combination of the first lens and the first portion of the housing shell defining a front optical imaging system, wherein the front optical imaging system has a first optical axis and a front field of view (FFOV) and is configured to form a first image at the optical detector system,
   wherein the first lens includes a first sequence of two meniscus lens elements, an optical doublet, and a first positive lens element separating said first sequence from said optical doublet, and
   wherein none of lens elements from the first lens includes an aspherical surface,
   a second lens facing a second portion of the housing shell that has a second non-zero optical power, a combination of the second lens and the second portion of the housing shell defining a lateral optical imaging system, wherein the lateral optical imaging system has a second optical axis and a lateral field of view (LFOV) and is configured to form a second image at the optical detector system.

2. An optoelectronic system according to claim 1, wherein at least one of the following conditions is satisfied: a) the optoelectronic system comprises a tether electrically connecting contents of the housing shell with a programmable processor outside of the housing shell in absence of an optical channel inside the tether, and b) the first and second lens are spatially separated by the optical detector system.

3. An optoelectronic system according to claim 2, wherein at least one of the following conditions is satisfied: (i) the tether includes only an electrically-conducting member and insulation for said electrically-conducting member, and (ii) the optical detector system includes only one optical detector.

4. An optoelectronic system according to claim 1,
   wherein the first image has a first perimeter that is a portion of a circumference of a circle, said circle including an axial point of the first image and having a first radius, wherein the second image is dimensioned as a stripe or band having a second perimeter that is a portion of a circumference of a circle with a second radius, and wherein the second radius is no smaller than the first radius,
   the optoelectronic system comprising:
   programmable electronic circuitry in electrical cooperation with the optical detector system, said programmable electronic circuitry configured to govern the operation of the optical detector system and, when the optical detector system includes only one optical detector, transform a chosen image of the first and second images to form a third image such that a remaining image of the first and second images and the third image having equal directionality.

5. An optoelectronic system according to claim 1, configured to form
   the first image that is optically-conjugate to a portion of an object space covered by the FFOV, the first image having a first perimeter that is a portion of a circumference of a circle, said circle including an axial point of the first image and having a first radius,
   the second image that is optically-conjugate to a portion of the object space covered by the LFOV, the second image being dimensioned, when the optoelectronic system is rotated in operation thereof about the shell axis, as an annulus having a second perimeter that is a portion of a circumference of a circle with a second radius, the second radius being no smaller than the first radius, and
   wherein a first directionality of the first image and a second directionality of the second image are equal to one another.

6. An optoelectronic system according to claim 1, wherein the second lens includes a second sequence of a meniscus lens element and a second positive lens element.

7. An optoelectronic system according to claim 6, wherein two optical surfaces of the second lens are aspheric al surfaces.

8. An optoelectronic system according to claim 7, wherein an optical lens element having a first of said two optical surfaces and an optical lens element having a second of said two optical surfaces are separated by a positive lens element.

9. An optoelectronic system according to claim 6, including a stop aperture between the first sequence of the two meniscus lens elements and the optical doublet.

10. An optoelectronic system according to claim 1, wherein the optical detector system includes spatially distinct first and second optical detectors, and wherein the front optical imaging system is configured to form the first image at the first optical detector and the lateral optical imaging system is configured to form the second image at the second optical detector.

11. A method for forming an image of an object space with the use of an optoelectronic system, the method comprising:
   acquiring, with an optical detector system located inside a housing shell of the optoelectronic system that has a shell axis, a first light through a first portion of the housing shell that has a first non-zero optical power and through a first lens, wherein a first combination of the first portion of the housing shell and the first lens defines a front optical imaging system of the optoelectronic system having a front field-of-view (FFOV),
wherein the first lens includes a first sequence of two meniscus lens elements, an optical doublet, and a first positive lens element separating said first sequence from said optical doublet, and wherein none of lens elements of the first lens includes an aspherical surface,
receiving, at the optical detector system, a second light through a second portion of the housing shell that has a second non-zero optical power and through a second lens, wherein a second combination of the second portion of the housing shell and the second lens defines a lateral optical imaging system of the optoelectronic system having a lateral field-of-view (LFOV);
wherein the first and second portions of the housing shell are integrally connected with one another to form a wall of the housing shell that encapsulates and fluidly seals the optical detector system and the first and second lenses,
forming a first image of a first portion of the object space covered by the FFOV from a first output provided by the optical detector system, the first image having a first perimeter that is a portion of a circumference of a circle, said circle including an axial point of the first image and having a first radius, the first image having a first directionality; and
forming a second image of a second portion of the object space covered by the LFOV from a second output provided by the optical detector system, the second image having a second directionality that is equal to the first directionality.

12. A method according to claim 11, wherein forming the second image includes forming the second image dimensioned as a stripe or band having an inner perimeter and an outer perimeter, the inner perimeter being a portion of a circumference of a circle with a second radius, the outer perimeter being a portion of a circumference of a circle with a third radius, wherein the second radius is no smaller than the first radius and the third radius is larger than the second radius.

13. A method according to claim 12, comprising rotating the housing shell about the shell axis by moving a tether that is connected to the housing shell and that is devoid of any optical member therein, to dimension said second image as an annulus having said second perimeter and circumscribing the first image.

14. A method according to claim 12, comprising at least one of the following actions:
a) transmitting electrical signals representing output from the optical detector system through a tether, which is connected to the housing shell and which is configured to transmit only electrical signals;
b) forming an auxiliary image of the second portion of the object space covered by the LFOV, the auxiliary image having an auxiliary directionality that is opposite to the first directionality;
c) transforming irradiance distribution of the auxiliary image to create said second image by radially redistributing irradiance of the auxiliary image with respect to a circumference of a circle of a chosen radius located between the inner and outer perimeters of said auxiliary image; and
d) with the use of programmable electronic circuitry of the optoelectronic system, generating a report containing a visually-perceivable representation of at least one of the first image and the second image.

15. A method according to claim 14,
wherein said irradiance distribution of the auxiliary image includes a first irradiance at a first image pixel at a first location outside of said circumference and a second irradiance at a second image pixel at a second location inside said circumference, the first and second locations being radially-symmetric with respect to the circumference with said chosen radius, wherein said chosen radius is defined as a weighted combination of (i) a geometric mean of the second and third radii, and (ii) an arithmetic mean of said second and third radii, and
wherein the transforming said irradiance distribution includes assigning a value of the first irradiance to the second image pixel while assigning a value of the second irradiance to the first image pixel.

16. A method according to claim 11, wherein at least one of the following conditions is satisfied:
a) said acquiring includes acquiring the first light at a first optical detector structured to collect light from the object space only through the front optical imaging system; and
b) said receiving includes receiving the second light at a second optical detector structured to collect light from the object space only through the lateral optical imaging system.

17. A method according to claim 16, wherein the first lens and the second lens are spatially separated from one another by at least one of the first optical detector and the second optical detector.

18. A method according to claim 11, wherein said acquiring includes transmitting the first light through a sequence of three meniscus lens elements prior to transmitting said first light through an optical doublet, wherein the first lens comprises two of said three meniscus lens elements and said optical doublet.

19. A method according to claim 18, wherein said acquiring comprises transmitting the first light through a stop aperture separating said optical doublet from a positive lens element.

20. A method according to claim 11, wherein said receiving includes transmitting the second light through a sequence of two positive lens elements after transmitting said second light through a sequence of two meniscus lens elements, wherein the second lens comprises one of said two meniscus lens elements and said sequence of two positive lens elements.

* * * * *